US011266458B2

(12) United States Patent
Perron et al.

(10) Patent No.: US 11,266,458 B2
(45) Date of Patent: Mar. 8, 2022

(54) CRYOSURGICAL SYSTEM WITH PRESSURE REGULATION

(71) Applicant: Galil Medical Inc., Arden Hills, MN (US)

(72) Inventors: Ted Jerome Perron, White Bear Lake, MN (US); Sean M. Morgan, Golden Valley, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 244 days.

(21) Appl. No.: 16/389,343

(22) Filed: Apr. 19, 2019

(65) Prior Publication Data

US 2019/0328437 A1 Oct. 31, 2019

Related U.S. Application Data

(60) Provisional application No. 62/663,808, filed on Apr. 27, 2018.

(51) Int. Cl.
A61B 18/02 (2006.01)
A61B 18/00 (2006.01)

(52) U.S. Cl.
CPC .... *A61B 18/02* (2013.01); *A61B 2018/00744* (2013.01); *A61B 2018/0262* (2013.01)

(58) Field of Classification Search
CPC .......... A61B 18/02; A61B 2018/00744; A61B 2018/0262; A61B 2018/00577; A61B 2018/00666; A61B 2018/0268; A61B 2018/0293; A61B 2090/064; F25D 29/00; A25D 29/001; F29B 9/02
See application file for complete search history.

(56) References Cited

U.S. PATENT DOCUMENTS

| 5,108,390 A | * | 4/1992 | Potocky | A61B 18/02 606/21 |
| 6,468,268 B1 | * | 10/2002 | Abboud | A61B 18/02 606/20 |
| 7,938,822 B1 | | 5/2011 | Berzak et al. | |
| 8,066,697 B2 | | 11/2011 | Zvuloni et al. | |
| 9,078,733 B2 | | 7/2015 | Ramadhyani et al. | |
| 2010/0256620 A1 | | 10/2010 | Maytal | |

(Continued)

FOREIGN PATENT DOCUMENTS

| CN | 106806013 A | 6/2017 |
| WO | 2014/189601 A1 | 11/2014 |
| WO | 2016/077045 A1 | 5/2016 |

OTHER PUBLICATIONS

"Visual Ice Cryoablation System," User Manual, Galil Medical Inc., Mar. 2015, 104 pages.

(Continued)

*Primary Examiner* — Linda C Dvorak
*Assistant Examiner* — Lindsay Regan Lancaster
(74) *Attorney, Agent, or Firm* — Faegre, Drinker, Biddle & Reath LLC

(57) ABSTRACT

A surgical cryoablation system comprising a valve having a valve inlet and a valve outlet the valve inlet connectable to a source of cryogenic fluid at a pressure of greater than 4000 psi and the valve outlet connectable to a cryoablation probe, such that the valve outlet is in fluid communication with the cryoprobe such that the source of cryogenic fluid is in fluid communication with the valve inlet.

22 Claims, 10 Drawing Sheets

(56) References Cited

U.S. PATENT DOCUMENTS

| | | | | |
|---|---|---|---|---|
| 2012/0059364 A1* | 3/2012 | Baust | ............... | A61B 18/02 |
| | | | | 606/24 |
| 2012/0265452 A1* | 10/2012 | Ramadhyani | ......... | A61B 18/02 |
| | | | | 702/47 |
| 2014/0046312 A1* | 2/2014 | Ramadhyani | ........ | A61F 7/0085 |
| | | | | 606/25 |
| 2015/0250524 A1* | 9/2015 | Moriarty | ............... | A61B 18/02 |
| | | | | 606/23 |
| 2015/0342660 A1* | 12/2015 | Nash | ............... | A61B 17/8855 |
| | | | | 606/21 |
| 2018/0028250 A1* | 2/2018 | O'Connor | ............. | A61H 39/06 |
| 2020/0360070 A1 | 11/2020 | Niedbala et al. | | |

OTHER PUBLICATIONS

Goulet et al., "Medical Device Console," Unpublished Design U.S. Appl. No. 29/647,802, filed May 15, 2018, 12 pages.

Parks et al., "Medical Device Console," Unpublished Design U.S. Appl. No. 29/647,670, filed May 15, 2018, 12 pages.

International Search Report and Written Opinion received for PCT Patent Application No. PCT/IB2019/053192, dated Aug. 7, 2019, 17 pages.

* cited by examiner

CRYOSURGICAL SYSTEM WITH PRESSURE REGULATION

CROSS REFERENCE TO RELATED APPLICATION

This application claims the benefit of U.S. Provisional Patent Application No. 62/663,808, filed Apr. 27, 2018, and titled "CRYOSURGICAL SYSTEM WITH PRESSURE REGULATION, the entire content of which is incorporated herein by reference.

BACKGROUND

Cryosurgical systems can be used for cryoablating target tissues (e.g., a tumor). During cryosurgery, for instance, a surgeon may deploy one or more surgical tools, such as cryoprobes to cryoablate a target area of a patient anatomy by placing the cryoprobe at or near the target area of the patient anatomy. In one example, a cryoprobe utilizes the Joule-Thomson (J-T) effect of a heat transfer medium or fluid supplied under pressure to produce cooling. Expansion of the pressurized cryofluid as it passes through a J-T orifice results in temperatures at or lower than those necessary for cryoablating a tissue in the vicinity of the tip of the cryoprobe. Heat transfer between the expanded cryofluid and the outer walls of the cryoprobe can be used to form an iceball, and consequently cryoablate the tissue.

In cryosurgical systems, the cryofluid may be supplied to the cryoprobes at a pressure which causes freezing of tissue during a freezing procedure and supplied at a lower pressure for thawing tissue during a thawing procedure. There may be one or more cycles of freezing and thawing during a cryoablation procedure.

Cryosurgical systems include one or more cryoprobes connected to one or more cryofluid sources. Such systems are described in the commonly-assigned patent, U.S. Pat. No. 8,066,697 and in published application, U.S. Pub. No. 2010/0256620 A1, the contents of which are hereby incorporated by reference in its entirety. Such systems provide separate supply and pressure control systems for high and low pressure cryofluids and so are relatively heavy, bulky and more expensive to produce.

SUMMARY

Systems and methods disclosed herein provide a heat transfer medium, such as a cryofluid (liquid/gas) to transfer heat between a surgical tool and surrounding tissue of a patient during a surgical procedure. The systems and methods disclosed herein permit pressure regulation of the heat transfer medium during the surgical procedure.

In an embodiment, the pressure regulation system includes a pressure control valve that can be actuated to an open state to permit passage of a heat transfer medium therethrough toward a surgical tool. The pressure control valve can be actuated to a closed state so as to restrict the passage of the heat transfer medium therethrough. It is preferred that the pressure regulation system includes a control system that controls actuation of the pressure control valve according to one or more control algorithms.

A further embodiment provides a first control algorithm for use in actuation of the pressure control valve to open and closed states. The control algorithm can, for example, be executed by the control system. The control system can, according to the first control algorithm, determine whether the pressure of the heat transfer medium is less than a minimum set-point pressure, and if so, output a first signal to a valve actuator to open the pressure control valve. The control system can, according to the first algorithm, also determine, whether the pressure of the heat transfer medium is above a maximum set-point pressure, and if so output a second signal to a valve actuator to close the pressure control valve.

In a further optional embodiment, after the pressure control valve is closed, the pressure may not decrease, and may continue increasing initially before decreasing. In such optional embodiments, the control algorithm can include a second control algorithm that can perform substantially the same steps as the first control algorithm, but additionally, determine, whether the pressure of the heat transfer medium reaches and/or exceeds a first pressure after the pressure control valve is closed. If so, the second control algorithm can advantageously adjust the minimum pressure set-point by an offset.

In further optional embodiments, the offset can be equal to a difference between the first pressure and the maximum pressure set-point and the minimum pressure set-point can be lowered by an amount generally equal to the calculated offset.

According to the second control algorithm, the subsequent opening of the valve can be adjusted by determining, after the pressure control valve is closed and prior to the subsequent opening of the pressure control valve, whether the pressure of the heat transfer medium is at or less than a second pressure, corresponding to the adjusted value of the minimum pressure set-point. If so, the second pressure, send a third signal to open the pressure control valve.

In further optional embodiments, the first pressure is, optionally, greater than maximum pressure set-point. Such an embodiment, in effect, may permit the opening and closing of the pressure control valve to include control system effects (for example, built-in delays, pressure blockages, etc.) and permit controlling the pressure of the heat transfer medium to generally equal a desired nominal pressure.

In a further optional embodiment, the control system can automatically indicate a fault condition if the pressure control valve is not closed in response to the second signal.

In one such optional embodiment, the elapsed time after the pressure control valve is opened can be compared to a predetermined time. If the pressure control valve remains open beyond the predetermined time, the pressure control valve can be closed and/or a fault condition can be generated. Preferably, the predetermined time can be greater than the time over which the pressure control valve remains open when controlled according to the first and/or second algorithms.

In a further preferred embodiment, in the absence of a fault condition, the pressure control valve is in the open state for a first duration. In such embodiments, the predetermined time is greater than the first duration.

A surgical system, such as a cryosurgical system, may comprise such an embodied pressure regulation system which in use is connected to convey a heat transfer medium from a source to a surgical tool.

In a further embodiment, there is provided a cryosurgical system comprising a pressure regulation system for performing one or more cryosurgical procedures (cryoablation, cryogenic freezing followed by thawing, cautery, etc.) The cryosurgical system can have at least one cryoprobe with a distal operating tip located in a distal section. The cryoprobe can receive a heat transfer medium for performing a cryosurgical procedure. The pressure control valve can be fluidly coupled to the cryoprobe and can regulate the pressure of the heat transfer medium supplied to the cryoprobe so as to permit uniform heat transfer between at least the distal section of the cryoprobe.

Optionally, the pressure regulation of heat transfer medium may only be performed during thawing following a freezing operation. In such embodiments, the control system can determine whether the cryosurgical system is performing a freeze operation, a thaw operation or a cautery operation, for example, based on an operator input.

In further embodiments, the heat transfer medium can be in a cryogenic state at the distal tip to freeze and/or cryogenically ablate tissue surrounding the cryoprobe during a freeze operation. The heat transfer medium can be in a non-cryogenic state at the distal tip during a thaw operation (or a cautery operation).

In an optional embodiment, the heat transfer medium can be argon. The heat transfer medium can be at a pressure of about 3500 psi (about 250 bar) upstream of the one or more pressure control valves, and expand from the pressure of about 3500 psi when reaching the distal tip of the cryoprobe to produce iceballs and/or to cryoablate tissue.

In a further optional embodiment, the heat transfer medium can be argon and can be regulated to a pressure of between about 200 psi (about 14 bar) and about 1000 psi (about 70 bar) starting from a pressure of about 1000 psi to about 4000 psi. In such embodiments, the pressure of argon upstream of the pressure control valve can be 3500 psi, and when pressure regulation is performed using one or more of the control algorithms disclosed herein, can be at a pressure of between about 200 psi and about 1000 psi.

In further optional or additional embodiments, multiple cryoprobes can each be connected to a pressure control valve (for example by a manifold design). In such embodiments, each cryoprobe can be independently operable relative to other cryoprobes, such that the control system can determine the maximum pressure set-point and the minimum pressure set-point corresponding to each cryoprobe, and open and close the pressure control valve connected to each cryoprobe based on the corresponding maximum pressure set-point and the minimum pressure set-point.

In further optional embodiments, each pressure control valve is electrically actuable, for example, a solenoid valve. In such cases, the control system is in electrical communication with each pressure control valve.

In further optional embodiments, each cryoprobe comprises an electrical heater for providing heat during the thaw operation. In such cases, the heat transfer medium can distribute heat generated by the electrical heater during the thaw operation.

In further optional aspects, a quantity of heat transfer medium flowing through the pressure control valve in the closed state can be less than a quantity of heat transfer medium flowing through the pressure control valve in the open state and thus, opening and closing the pressure control valve according to control algorithms may, in effect, vary the pressure of the heat transfer medium flowing through the pressure control valve.

The pressure regulation system can, in further optional aspects, include a pressure transducer to measure and/or monitor a pressure of the heat transfer medium. In an optional embodiment, the pressure transducer can be positioned at the outlet or downstream of the outlet of the pressure control valve.

In an embodiment, a surgical system comprises a pressure regulation system for regulating the pressure of a heat transfer medium conveyed from a source of heat transfer medium to a surgical tool at a pressure for causing freezing in a freezing procedure and at a lower pressure for thawing in a thawing procedure, the pressure regulation system comprising: a valve arrangement comprising a pressure control valve and an actuator for actuating the valve to an open and a closed state, wherein in an open state the valve allows heat transfer medium flow to a surgical tool and in a closed state the valve resists heat transfer medium flow to a surgical tool; and a controller operably connected to the valve arrangement for causing selective actuation of the valve to the open and the closed states, wherein in a thawing procedure the controller is responsive to a determined pressure of the heat transfer medium downstream of the valve arrangement to cause actuation of the valve to an open state when the determined pressure is less than a lower set-point pressure value and to cause actuation of the valve to a closed state when the determined pressure is higher than an upper set-point pressure value thereby generating a thawing pressure which cycles between the set-point pressure values for conveying a pressure over time which is less than the pressure for causing freezing.

This pressure range may be adjusted by an adjustment value if it is determined for example by a pressure sensor that the pressure exceeds the range and then the adjustment value may be reduced over multiple thawing pressure cycles. During thawing when fluid pressure is regulated so as not to cause freezing a heater may heat the fluid for transferring heat energy for thawing frozen tissue.

The details of one or more examples are set forth in the accompanying drawings and the description below. Other features, objects, and advantages will be apparent from the description and drawings, and from the claims.

DETAILED DESCRIPTION

Figure 1:
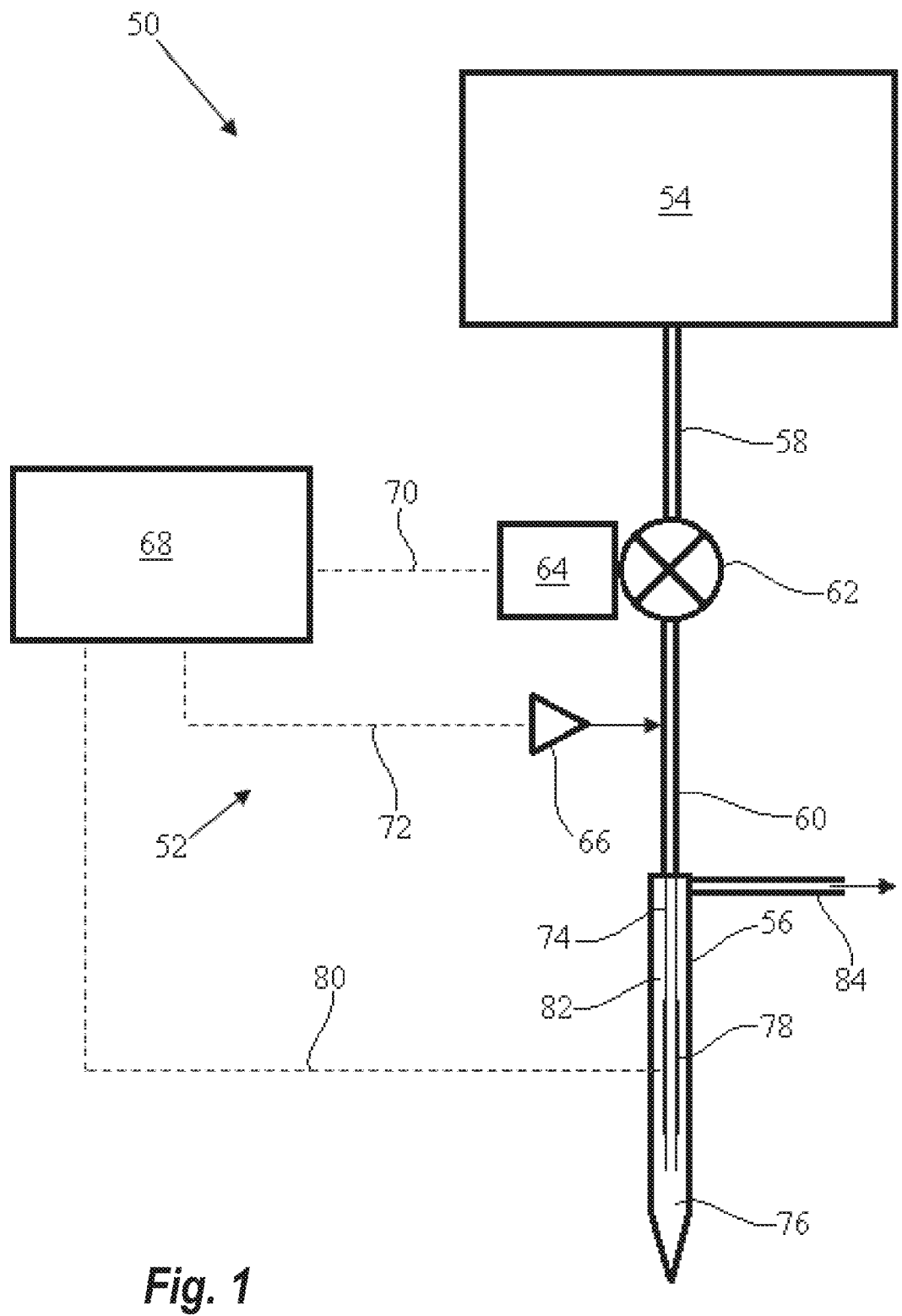
FIG. 1 is a schematic illustrating a surgical system according to a non-limiting exemplary embodiment.

Referring to FIG. 1 there is shown an example of a surgical system 50 comprising a pressure regulation system 52 for regulating the pressure of a heat transfer medium or fluid supplied from a fluid source 54 to a surgical tool 56. In a cryoablation surgical system, the surgical tool is a cryoablation probe for receiving fluid at a pressure for causing freezing in a freezing procedure and at a lower pressure for thawing in a thawing procedure.

The source of fluid may be a pressurized vessel for containing fluid under a required pressure or a supply line in a hospital for supplying fluid at a required pressure from a remote source. The pressure regulator is arranged for connection by fluid lines 58, 60 to the fluid source and the surgical tool for regulating the pressure at which fluid is conveyed to the surgical tool from the source. The pressure regulator comprises a valve arrangement including a valve 62 and a valve actuator 64 for actuating the valve to an open state which allows fluid flow to the surgical tool and a closed state which restricts fluid flow. A pressure transducer, or sensor, 66 is arranged to determine or measure the pressure of fluid flowing to the surgical tool downstream of the valve and is operably connected to the controller for outputting a signal corresponding with the determined pressure.

A controller 68 of the pressure regulation system is connected by a control line 70 to the pressure regulator. In a cryogenic or freezing procedure the controller causes actuation of the valve to the open state allowing fluid flow at a pressure which is suitable for generating a cryogenic temperature in the surgical tool (a cryogenic generating pressure). This pressure may be generally the same pressure at which the fluid is stored subject to pressure losses in the system. In a thawing procedure, the controller controls the pressure regulator so that fluid flow to the surgical tool is at a reduced pressure lower than the cryogenic generating pressure. The lower pressure reduces the temperature applied by the surgical probe.

The controller is connected to the pressure transducer by control line 72 and is arranged to receive an output from the pressure transducer 66 corresponding to the pressure determined by the transducer. The controller causes selective actuation of the valve 62 responsive to the determined pressure.

In order to reduce pressure in a thawing procedure, the controller 68 causes actuation of the valve 62 to open and closed states at respective lower and upper set-point pressure values for generating a thawing pressure which cycles between the set-point pressure values for conveying a pressure over time which is less than the pressure for causing freezing (the cryogenic generating pressure). The target pressure over time is the average effective pressure and is between the lower and upper set-point pressure values. The set-point pressure values are predetermined so that flow pressure is lower than the cryogenic generating pressure and are dependent on the selected heat transfer medium and other characteristics of the system. At least the lower set-point value is less than the cryogenic generating pressure and preferably both of the lower and upper set-point pressure values are less than the cryogenic generating pressure.

The set-point pressure values may be adjusted by the controller during operation in the event that the pressure exceeds the set-point pressure values (or range of acceptable pressure values), particularly during thawing if flow pressure is higher than required. If in a thawing pressure cycle pressure exceeds the upper set-point pressure value adjustment is made to compensate. There are a number of reasons for the cause of this over-pressure as explained in more detail below.

In one example, the controller is arranged to adjust the lower set-point pressure value by an adjustment value if the pressure exceeds the upper set-point pressure value during a thawing pressure cycle and to cause actuation of the valve to an open state at the adjusted lower set-point pressure value. This adjustment allows the pressure to decrease during a thawing pressure cycle to a pressure which is less than the lower set-point pressure value to compensate for a pressure which exceeds the upper set-point pressure value. The adjustment between the lower set-point pressure value and the adjusted set-point pressure value may be equal to the difference between the over-pressure and the upper set-point pressure value.

In another example, the controller is arranged to adjust the upper set-point pressure value by an adjustment value for a thawing pressure cycle if the pressure exceeds the upper set-point pressure value during a preceding thawing pressure cycle and to cause actuation of the valve to a closed state at the adjusted upper set-point pressure value. The adjustment to the upper set-point pressure value may be equal to the difference between the over-pressure and the upper set-point pressure value.

Figure 9:
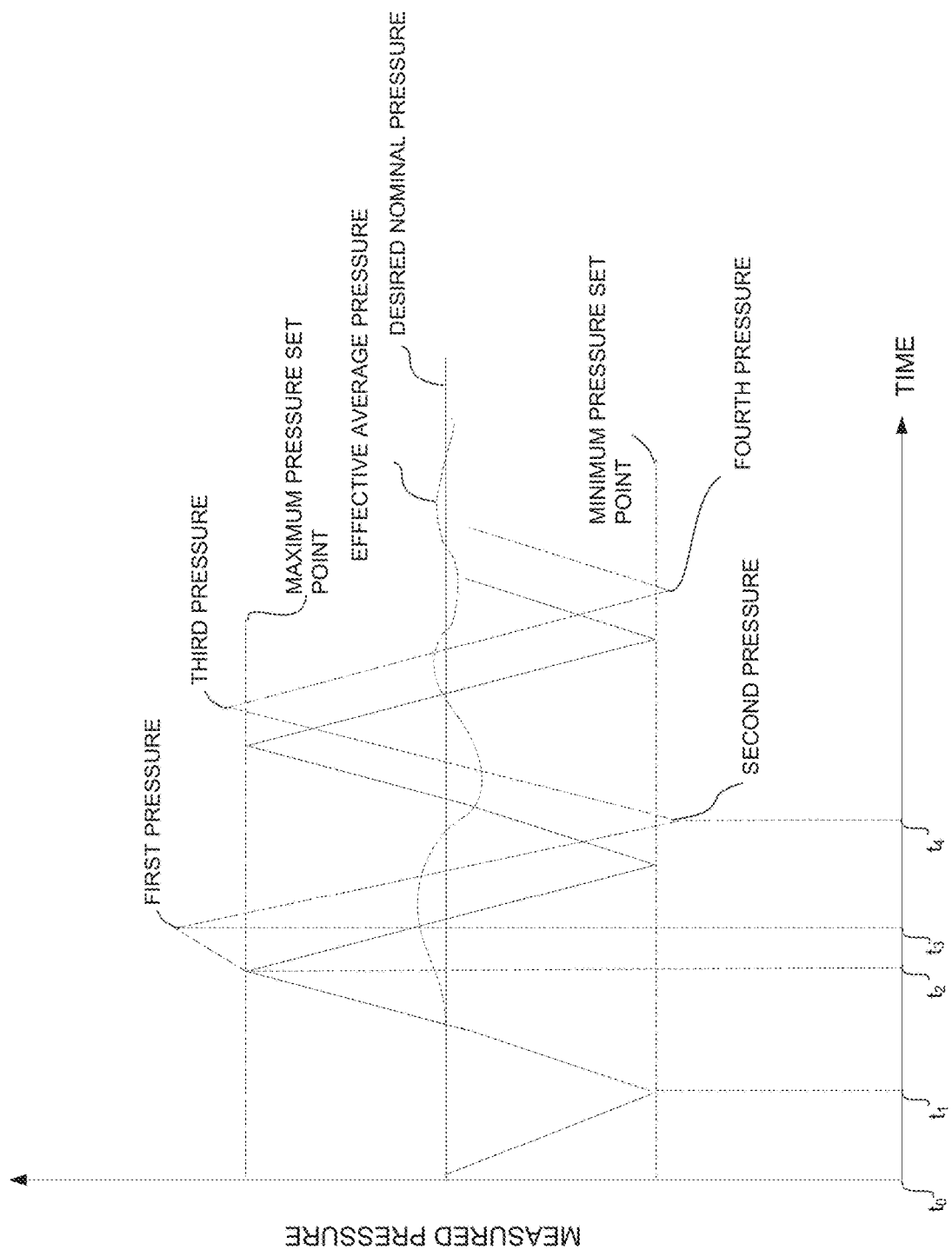
FIG. 9 is an illustration of pressure of the heat transfer medium as measured by the pressure transducer when the control algorithms of FIGS. 7 and 8 are implemented.

The adjustment values are reduced over multiple thawing pressure cycles so that over time the adjusted upper and lower set-point pressure values align with the upper and lower set-point pressure values for generating a target thawing pressure as an effective average between the upper and lower set-point pressure values. Preferably one or both adjustment values are reduced one cycle compared to a previous consecutive cycle. The graph in FIG. 9 shows an example of the pressure cycle during adjustment as the effective average pressure gradually aligns with the desired or target nominal pressure.

The surgical tool 56 comprises a supply tube 74. Pressurized fluid in the supply tube undergoes Joule-Thomson expansion into an expansion region 76 of the tool causing cooling. When the fluid pressure is sufficiently high expansion causes temperatures which are suitable to freeze tissue. The surgical tool comprises a heater 78 for heating fluid in the supply tube during a thawing procedure. During thawing the fluid is regulated to a lower pressure and does not cause significant cooling, which would otherwise counteract the heat supplied by the heater. The controller 68 is operably connected to the heater by control line 80. The controller outputs a signal to the heater to cause heating when thawing is required.

The supply tube 74 is spaced from an inner housing wall of the surgical tool to define a fluid passage 82 for conveying fluid away from the expansion region to an exhaust 84, either for recirculation to the fluid source, or exhausting to atmosphere or for containment.

In the following description there are described further examples of a surgical system, such as a cryosurgical system, including more detailed explanation and numerous modifications which may be included in the above example or other examples. For instance, any aspect of the disclosure relating to pressure regulation system 200 described below apply also to pressure regulation system 52 described above and similarly to control systems 68 and 310.

Figure 2:
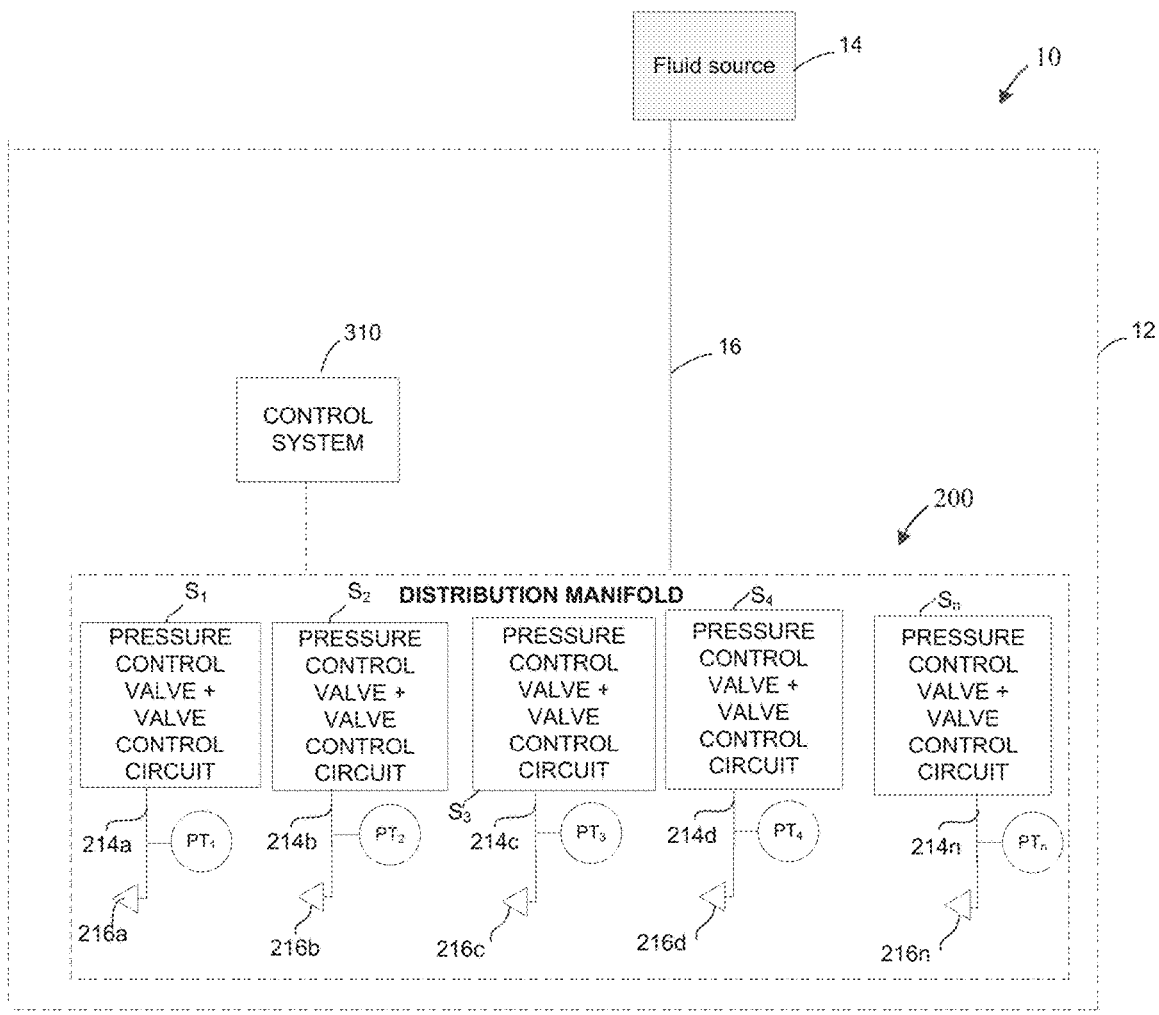
FIG. 2 is a schematic illustrating a cryosurgery system according to a non-limiting exemplary embodiment.

Referring to FIG. 2, a pressure regulation system 200 is shown for a surgical system. The surgical system can be a cryosurgical system. However, it should be understood that the pressure regulation system 200 is not limited to the cryosurgical system.

Overall System

FIG. 2 is a schematic of a cryosurgery system 10. Components of the system can be compactly packaged inside a system housing 12. The cryosurgical system comprises one or more fluid sources 14. The fluid sources 14 can supply a heat transfer medium, or fluid, during cryosurgery. For example, the heat transfer medium can be fluids such as argon, nitrogen, air, krypton, CO2, CF4, xenon, and various other gases. In an example, the fluid source 14 can simply be a pressurized vessel or canister. In certain advantageous aspects, the cryosurgery system 10 can be in the form of a portable desktop console. In some such advantageous aspects, the system may have a weight of less than about 50 pounds (e.g., about 44 pounds). Accordingly, such systems can be compactly positioned in the surgery room thereby reducing space requirements.

Figure 3:
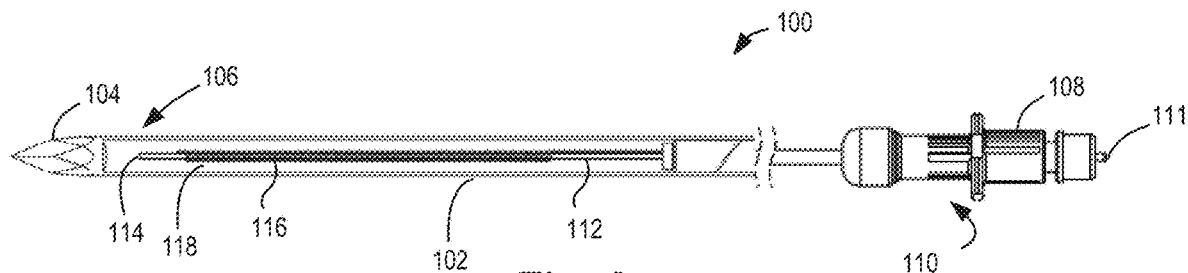
FIG. 3 is a sectional front view of a cryoprobe according to a non-limiting exemplary embodiment.

The cryosurgery system 10, illustrated in FIG. 2 includes a pressure regulation system 200 that can regulate a pressure of the heat transfer medium supplied from the fluid source 14 to a surgical tool (shown in FIG. 3). As seen from FIG. 2, the pressure regulation system 200 includes one or more pressure control valves in fluid communication with the fluid source 14. The pressure regulation system 200 includes a control system 310 for controlling actuation of pressure control valves $S_1$, $S_2$, $S_3$, $S_4$, $S_n$ according to one or more algorithms, as will be described further below.

Continuing with FIG. 2, the heat transfer medium can be conveyed from the fluid source 14 via a fluid source outlet 16 toward a pressure regulation system 200 as will be described further below. Heat transfer medium within the fluid source 14 can be at pressures well-above the desired pressure. For instance, a pressure of the heat transfer medium at the fluid source outlet 16 can be about 3500 psi (about 240 bar) or in the range between about 1000 psi (about 69 bar) and about 4000 psi (about 275 bar). The fluid source 14 may be a pressurized vessel or container (e.g., a gas cylinder) containing a heat transfer medium at pressures well above the pressure at the fluid source outlet 16 for instance between about 5000 psi (about 350 bar) and about 7000 psi (about 480 bar). Accordingly, the pressure of the heat transfer medium is reduced to a desired level by inclusion of a pressure regulator. Heat transfer medium just downstream (e.g., as the fluid travels toward the cryoprobe) of the pressure regulator can be at a pressure lower than the pressure at the fluid source outlet 16. For example, in some cases, the pressure regulator can reduce the pressure of the heat transfer medium to less than about 4000 psi (about 275 bar) (e.g., about 3500 psi or 240 bar). Optionally, a pressure transducer can be fluidly coupled to the pressure regulator to measure pressure of the heat transfer medium of the fluid source 14.

The system shown in FIG. 2 can be of a "closed-loop" type. One such system is described in the commonly-assigned application titled, "Closed-Loop System for Cryosurgery," and granted as U.S. Pat. No. 9,078,733 B2, the entire contents of which is hereby incorporated by reference. In an embodiment of a closed loop system, heat transfer medium is not exhausted to the surroundings after a surgical procedure (e.g., cryosurgery) is completed. Instead, the heat transfer medium is returned (e.g., by a return pathway) from the flow channels (channel 1, channel 2, channel 3, channel 4, etc. shown in FIG. 5) to the fluid source 14. Direction control valves (e.g., check valves) may be used to reduce and/or to prevent flow of the heat transfer medium in a direction other than the intended direction (e.g., flow toward the cryoprobe 100 or return flow from the cryoprobe 100).

Cryoprobe

As described earlier, the surgical tool may be a cryoprobe 100 such as the cryoprobe 100 shown in FIG. 3. The cryoprobe 100 comprises an elongate generally cylindrical hollow body or probe shaft 102. The shaft is illustrated in cross-section to show internal components (e.g., a trocar).

The probe shaft 102 is formed with an operating tip 104 disposed at a section 106 distal from a fluid or control connection for penetrating through tissues of a patient during deployment. A coupler 108 is located at a proximal section 110 opposite to the distal section 106. The coupler 108 comprises a pin 111 for connection to a control system 310 and/or source as will be described further below.

The probe shaft 102 can be of substantially small cross section for allowing deployment in tissues of a patient. In an example, the probe shaft 102 has an outer diameter of about 2.1 millimeters. Other dimensions of the probe shaft 102 are also contemplated. For example, the probe shaft 102 can have an outer diameter of between about 1.5 millimeters and about 2.4 millimeters. In addition, the operating tip 104 can be made of a pliant material so as to be flexible (e.g., relative to the proximal portion of the cryoprobe 100) for penetrating soft tissue.

As seen in FIG. 3, the cryoprobe 100 includes a supply tube 112 extending substantially along its length for providing a high-pressure heat transfer medium to the operating tip 104. The supply tube 112 can be positioned coaxially/concentrically within the probe shaft 102. The supply tube 112 can be configured to supply a heat transfer medium (e.g., cryofluid) for forming iceballs on an outer surface of the probe shaft 102 over the distal section 106. In some cases, the supply tube 112 can be a capillary tube.

The cryoprobe 100 may include a cryocooler as shown in FIG. 3. For instance, the supply tube 112 can terminate in a Joule-Thomson orifice 114. The Joule-Thomson orifice 114 can be positioned near the operating tip 104, so as to permit heat transfer medium exiting the Joule-Thomson orifice 114 to expand into an expansion chamber for cooling the distal section 106 and particularly the operating tip. As the heat transfer medium expands in the expansion chamber, it cools rapidly and forms iceballs of different shapes and/or sizes over the outer surface of the distal section and operating tip 104. The expanded heat transfer medium in the expansion chamber is colder than the incoming heat transfer medium. The iceballs that are formed as a result of rapid expansion of the heat transfer medium can freeze and/or ablate tissue (e.g., a tumor).

While an exemplary cryocooler such as a Joule-Thomson orifice 114 is illustrated, it should be understood that other types of cryocoolers such as cryogenic dewars, Stirling-type cooler, pulse-tube refrigerator (PTR), Gifford-McMahon (GM) cooler are contemplated within the scope of the present disclosure. Further, as briefly noted above, cryofluids which may be used for cooling include argon, liquid nitrogen, air, krypton, $CF_4$, xenon, or $N_2O$.

The outer surface of the operating tip 104 can be made of a material having a high thermal conductivity, such as a metal or metal alloy for effectively conducting heat from the patient tissue. Stainless steel is a suitable example of such a material.

Referring again to FIG. 3, a heater 116 can optionally be provided within the probe shaft 102 to facilitate thawing and/or cauterizing tissue. The heater 116 may be operated after cooling and iceball formation to thaw frozen tissue. Optionally, the heater 116 may be operated after completion of a surgical procedure to facilitate disengagement of the cryoprobe 100 therefrom. As referred to herein, thaw/thawing may interchangeably refer to either of the two procedures, of thawing an iceball in between freeze operations, or operating the heater 116 to facilitate disengagement of the cryoprobe 100.

The heater 116 is arranged to heat the heat transfer fluid as it is conveyed through the supply tube 112 during a thawing part of a procedure. The heat transfer medium may be at conditions (pressure, temperature, phase, etc.) such that when expanding from the orifice 114, the heat transfer medium may not reach cryogenic temperatures at certain instances (described below). Instead, the heat transfer medium at these conditions functions to transfer heat to the distal section 108 and operating tip for thawing tissue. The heat transfer medium may itself be at a temperature sufficient for thawing or as shown may be heated by the heater 116 to raise the temperature.

An electrical heater 116 can be provided coaxially with the supply tube 112 and the probe shaft 102 to facilitate heating the distal section 106 of the cryoprobe 100. Alternatively, the electrical heater 116 can be positioned elsewhere in cryoprobe 100 to heat the distal section 106 of the cryoprobe 100. The electrical heater 116 can be a resistive heater 116, wherein the electrical heater 116 generates heat proportional to the current flow therethrough and the electrical resistance of electrical heater 116. In such cases, the probe is arranged to connect to a source of electrical power for conveying an electrical current to the heater 116.

As seen in the FIG. 3 example, the annular area between the supply tube 112 and the inner walls of the probe shaft 102 defines a return lumen 118 in fluid communication with the expansion chamber for conveying expanded heat transfer medium from the expansion chamber. In an example of a closed-loop system the heat transfer medium is returned to a fluid source after each surgical procedure. Alternatively, a system can be operated in an "open-loop" configuration, and can be exhausted to the surroundings after use.

Properties of Heat Transfer Medium

In certain examples of the system, the heat transfer medium can be at an initial state when entering the pressure regulation system 200. The initial state can be defined by an initial pressure and an initial temperature. The initial pressure and the initial temperature can be such that when the heat transfer medium undergoes expansion, (e.g., Joule-Thomson expansion through the orifice 114), the pressure and the temperature of the heat transfer medium may both decrease. When the heat transfer medium undergoes expansion from pressures significantly less than the initial pressure, however, a reduction in pressure may not be accompanied by a reduction in temperature (for instance, to cryogenic temperature). Thus, if it is desirable to provide the heat transfer medium to the distal section 108 in a cryogenic state, the pressure of the heat transfer medium entering the pressure regulation system 200 may not have to be substantially further reduced from the initial pressure. However, if heat transfer medium at a non-cryogenic state is to be provided to the distal section 108, the pressure of the heat transfer medium can be substantially reduced from the initial pressure by the pressure regulation system 200.

In examples of the system, as described above, if the initial pressure of the heat transfer medium is sufficiently high, the heat transfer medium undergoes expansion, and is cooled. The expansion of the heat transfer medium may cool the heat transfer medium sufficiently such that the temperature of the heat transfer medium reduces to cryogenic temperature. For simplicity this sufficiently high initial pressure is referred to as a cryogenic pressure and varies dependent on the medium (type of the heat transfer medium, such as a gas or liquid, temperature of the heat transfer medium prior to expansion, and the like) and other characteristics of the system. Therefore during a freezing procedure, the pressure regulator is arranged to supply a heat transfer medium at a cryogenic pressure taking into account that there are some pressure losses inherent in the system (e.g. between the pressure regulator and surgical tool).

During thawing, the pressure of the heat transfer medium is regulated so that it is less than the cryogenic pressure. Preferably the pressure is regulated so that it less than the cryogenic pressure by a safety margin. For simplicity this pressure is referred to as a non-cryogenic pressure. Expansion of the heat transfer medium (e.g., the same medium and under same characteristics as the freezing procedure) from the non-cryogenic pressure may not reduce the temperature of the heat transfer medium sufficiently to reach cryogenic temperatures.

In an example, the cryogenic pressure may be about 3500 psi (about 240 bar), and the heat transfer medium may be argon. The cryogenic temperature generated may be less than about 150 Kelvin and preferably in the range of 120 to 150 Kelvin. In a freezing procedure, as argon leaves the supply tube 112, it expands from the cryogenic pressure causing cooling, and reaches a cryogenic state. In a thaw procedure, the supply pressure of argon is regulated to a non-cryogenic pressure of less than about 1000 psi (about 70 bar), and preferably less than about 700 psi (about 48 bar). When argon undergoes expansion from this pressure, its temperature does not reduce significantly to reach cryogenic temperatures (or generally remains constant). Argon may remain at a temperature of above 150 K, and preferably above 273 K, and may continue to increase particularly when heated by the heater 116.

In this regard, the cryoprobe 100 can receive the heat transfer medium during the thaw procedure (or cautery). At this point, the heater 116 supplies heat to the probe shaft 102 to facilitate removal of the probe shaft 102 from the frozen tissue. Accordingly, in such embodiments, the heat transfer medium can evenly distribute the heat generated by the heater 116 over the surface area of the probe shaft 102, so as to permit uniform heat transfer rate between various points on the probe shaft 102 and the surrounding tissue. Such embodiments permit ease of removal of the probe shaft 102 from the tissue.

Referring back to FIG. 2, heat transfer medium is conveyed from a fluid source 14 to a pressure regulation system 200 for regulating the pressure of the heat transfer medium. One or more cryoprobes can be fluidly connected to and positioned downstream (e.g., as the fluid travels toward the cryoprobe) of the pressure regulation system 200 such that heat transfer medium at a desired pressure can be supplied to the supply tube 112. The pressure regulation system 200 can adjust the pressure of the heat transfer medium such that the heat transfer medium is in a cryogenic state during certain portions of a cryosurgical procedure and in a non-cryogenic state during certain other portions of the cryosurgical procedure.

For instance, the cryoprobe 100 can receive the heat transfer medium in a cryogenic state during the freeze cycle. Accordingly, the pressure regulation system 200 can be configured, as will be described below, to ensure that the heat transfer medium leaving the supply tube 112 is at the cryogenic pressure (e.g., 3500 psi for argon) during the freeze cycle. Further the cryoprobe 100 can receive the heat transfer medium in a non-cryogenic state during the thaw operation (and/or a cautery operation) to permit heat exchange between the cryoprobe 100 and the tissue surrounding the cryoprobe 100. Accordingly, the pressure regulation system 200 can be configured, as will be described further below, to ensure that the pressure of heat transfer medium downstream (e.g., as the fluid travels toward the cryoprobe) of the pressure regulation system 200 and/or as the heat transfer medium leaves the supply tube 112 is less than the non-cryogenic pressure (e.g., less than 1000 psi for argon). Advantageously, as described above, providing heat transfer medium in a non-cryogenic state during the thaw operation (or a cautery operation) permits evenly distributing heat generated by the heater 116 during the thaw operation (or a cautery operation) such that heat transfer between the probe shaft 102 and the surrounding tissue (as characterized, for example, by temperature of the probe shaft over a length of the probe shaft) during the thaw cycle (and/or cautery) is uniform. Such embodiments may improve ease of removal of the cryoprobe 100 once cryoablation is complete.

Pressure Regulation System

Common Inlet to Pressure Control Valves

Figure 4:
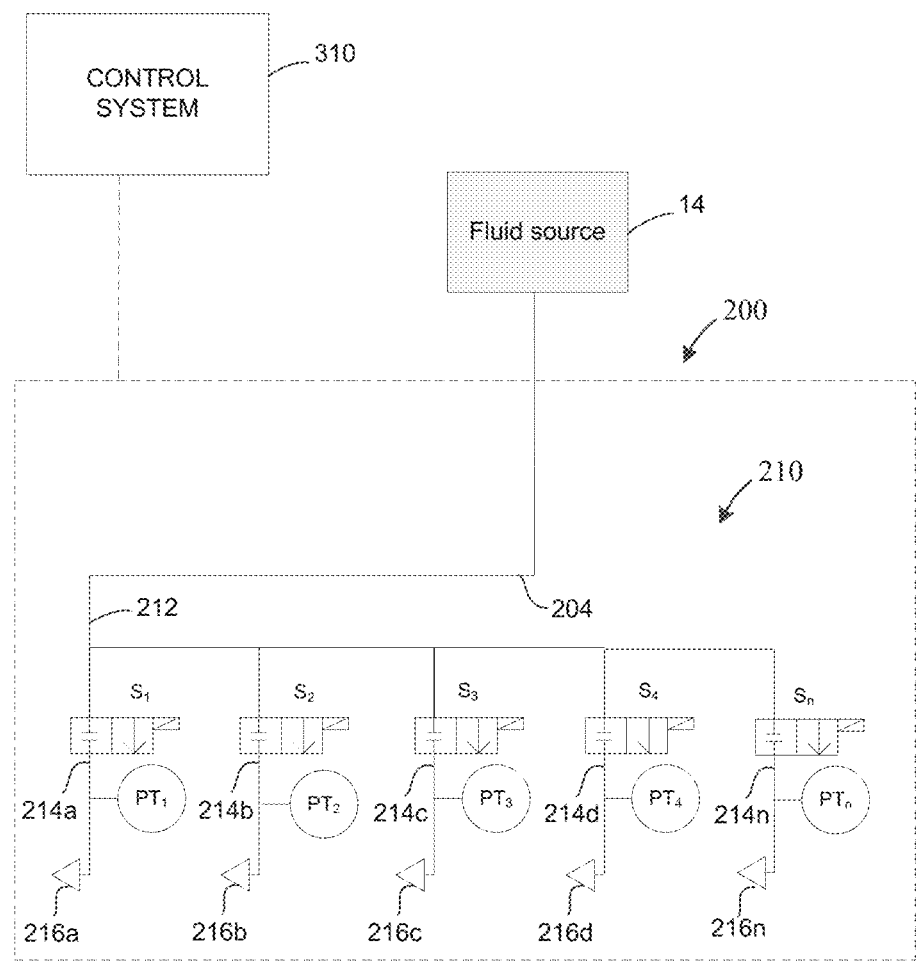
FIG. 4 is a schematic illustrating a pressure regulation system according to a non-limiting exemplary embodiment.

FIG. 4 is a schematic that illustrates the details of the pressure regulation system 200. In FIG. 4, the solid lines connecting various components can be fluid lines, or ducts, 204 (e.g., tubes) coupled to the components of the pressure regulation system 200 by fluid couplings (e.g., mechanical connectors).

As seen in FIG. 4, the pressure regulation system 200 includes a plurality of pressure control valves ($S_1$, $S_2$, $S_3$, $S_4$, . . . $S_n$) controlled by valve controllers. The valve controllers can be integrated into the pressure control valves ($S_1$, $S_2$, $S_3$, $S_4$, . . . $S_n$). The valve controllers can include electrical/electronic circuitry (e.g., diodes, field programmable gate arrays, printed circuit board (PCB) processors and the like) that can receive an electrical signal and/or instructions. The valve controller can optionally include an electromagnetic actuator that can be energized (e.g., by a voltage or current) or de-energized to move the pressure control valves ($S_1$, $S_2$, $S_3$, $S_4$, . . . $S_n$) between open and closed states.

In an embodiment, the pressure control valves ($S_1$, $S_2$, $S_3$, $S_4$, . . . $S_n$) can be configured and arranged in the form of a manifold design and may be referred to as a distribution manifold 210. Referring back to FIG. 2, according to an example, the distribution manifold 210 can be housed within the system housing 12.

In an example, as illustrated in FIG. 4, the distribution manifold 210 can optionally have a common manifold inlet 212 upstream of each pressure control valve S1, S2, S3, S4 and a plurality of valve outlets 214a, 214b, 214c, 214d, . . . 214n. Each valve outlet (214a, 214b, 214c, 214d, . . . 214n) is downstream (e.g., as the fluid travels toward the cryoprobe) of a corresponding pressure control valve ($S_1$, $S_2$, $S_3$, $S_4$, . . . $S_n$). One or more cryoprobes can be fluidly coupled to each valve outlet (214a, 214b, 214c, 214d, . . . 214n) via a corresponding flow channel (216a, 216b, 216c, 216d . . . 216n) as will be described further below. While four pressure control valves are illustrated, it should be understood that additional or fewer valves are contemplated within the scope of the present disclosure. In addition, configurations other than a manifold design for arranging and positioning the pressure control valves are also contemplated within the present disclosure.

As shown in FIG. 4, the common manifold inlet 212 can be fluidly coupled to the fluid line 16 that supplies the heat transfer medium. The fluid connections of the manifold inlet can permit the manifold inlet to be in direct or indirect fluid communication with the fluid source 14, and therefore receive heat transfer medium directly or indirectly therefrom.

Flow to Cryptoprobes and Return Flow

Figure 5:
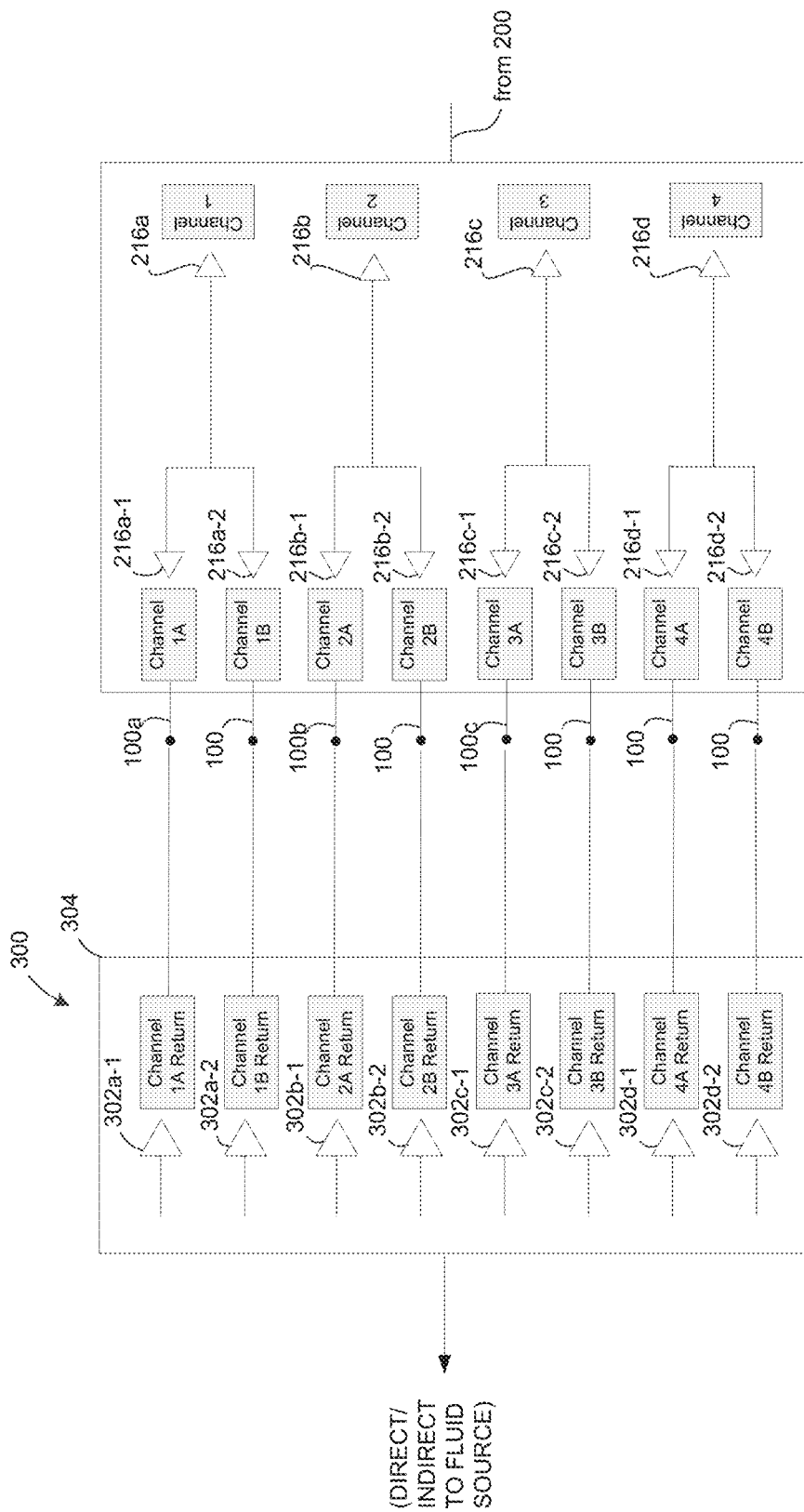
FIG. 5 is a schematic illustrating downstream connections of the pressure regulation system of FIG. 4.

FIG. 5 illustrates an example of a system for connection to a plurality of cryosurgical tools so that more than one tool can be used for performing a procedure. FIG. 5 shows the connections of each of the valve outlets (214a, 214b, 214c and 214d). In the illustrated embodiment, each flow channel (216a, 216b, 216c, 216d, . . . 216n) is connected to two sub-channels (216a-1, 216a-2, 216b-1, 216b-2, 216c-1, 216c-2, 216d-1, 216d-2), each being fluidly connectable with a cryoprobe 100. Accordingly, a single pressure control valve ($S_1$, $S_2$, $S_3$, $S_4$ . . . $S_n$ shown in FIG. 3) can be fluidly coupled to two cryoprobes according to the illustrated embodiment. Additional or fewer cryoprobes per pressure control valve ($S_1$, $S_2$, $S_3$, $S_4$, . . . $S_n$) are contemplated within the scope of the present disclosure. The sub-channels can be configured in the shape of a fluid port or connector so as to connect the distribution manifold 210 and components thereof to the proximal coupler 108 of the cryoprobe 100. For instance, the sub-channels can terminate in a connector that can engage with and connect to the proximal pin 111 of the proximal coupler 108. Advantageously, in addition to being fluidly connectable to the sub-channel, the proximal coupler 108 can electrically connect (e.g., via a BNC type electrical connector and/or electrical cables) the cryoprobe 100 with the control system 310 so as to permit the control system 310 to electrically communicate with the cryoprobe 100 before or during a cryosurgical procedure.

A pressure regulation system can include various optional flow conditioning components as explained with reference for example to FIG. 4 to ensure desired properties of the heat transfer medium entering the pressure control valves for various purposes, such as relieving excess pressure in fluid line 204 that conveys heat transfer medium if the pressure in the fluid lines 204 reach and/or exceed a limiting value of pressure. The limiting value of pressure can be chosen based on operating conditions as well as safety considerations. The pressure regulation system 200 can also optionally include a pressure transducer fluidly coupled to the fluid line 204 so as to monitor pressure of the heat transfer medium entering the pressure regulation system 200 and conveyed by fluid line 204. Further, optionally, pressure regulation system 200 can include a dryer that can be fluidly coupled to and positioned downstream (e.g., as the fluid travels toward the cryoprobe) of the pressure transducer. Optionally, each flow channel 216a, 216b, 216c, 216d (illustrated fluidly coupled to the valve outlet 214a, 214b, 214c, 214d in FIG. 3) can be fluidly coupled to one or more dryers (e.g., silica gel or other desiccants or dryers). In addition, in some cases, each sub-channel can have a direction control valve to reduce or prevent the chances of heat transfer medium from flowing other than in the intended direction (e.g., downstream toward the cryoprobe 100, or from the cryoprobe 100 back toward the fluid source 14 via a return path).

As mentioned previously, the system can be a closed-loop system, whereby the heat transfer medium, is not exhausted after use, and is instead returned to the fluid source 14. FIG. 5 illustrates one such return flow section 300 according to an embodiment. As seen in FIG. 5, the return flow section 300 can also be configured as a manifold, and can, in some embodiments, be referred to as a return manifold 304. The return manifold 304 can have return flow sub-channels (302a-1, 302a-2, 302b-1, 302b-2, 302c-1, 302c-2, 302d-1, 302d-2). In certain non-limiting embodiments, the number of return flow sub-channels (302a-1, 302a-2, 302b-1, 302b-2, 302c-1, 302c-2, 302d-1, 302d-2) can equal the number of flow sub-channels (216a-1, 216a-2, 216b-1, 216b-2, 216c-1, 216c-2, 216d-1, 216d-2). Each return flow sub-channel can be in the form of a fluid connection port and can be in fluid communication with the return lumen 118 of the cryoprobe 100.

Solenoid Valve Control

A pressure control valve for example as shown in FIGS. 1, 2 and 4 is associated with a valve control, or actuator, for causing actuation of the valve responsive to an output from a system control (e.g controller 68 or system control 310). The valve control may comprise a solenoid that causes or allows movement of a valve member for selective engagement with a valve seat. When the valve member is engaged with the valve seat flow through the valve is restricted (closed state) and when disengaged flow is permitted (open state). The valve controller can include, in one example, an electrical control circuit in communication with (e.g., receiving signals and/or instructions from) the control system for energizing a solenoid in response to an output signal from the control system. Other types of valves are contemplated within the scope of the present disclosure.

The pressure control valves ($S_1$, $S_2$, $S_3$, $S_4$, ... $S_n$) can be actuated to move the pressure control valve ($S_1$, $S_2$, $S_3$, $S_4$, ... $S_n$) between a closed state and an open state. In the open state, heat transfer medium received from the common manifold inlet may flow through the pressure control valve ($S_1$, $S_2$, $S_3$, $S_4$, ... $S_n$) and exit the pressure control valve via the valve outlet (214a, 214b, 214c, 214d, ... 214n), and flow toward the cryoprobe 100(s) fluidly coupled to the valve outlet (214a, 214b, 214c, 214d, ... 214n). The pressure control valves ($S_1$, $S_2$, $S_3$, $S_4$, ... $S_n$) can be normally in the closed state until they are actively energized (e.g., by an electrical signal or instructions sent from the control system 310) to move from the closed state to the open state.

In certain aspects, in the open state and in the closed state respectively, the pressure control valves may either be in a fully open and fully closed state or may be partially open and partially closed respectively. As used herein, the term "close," "closed," "closing," (or variations thereof) or "closed state" can include both a partially closed state and/or a fully closed state. Further, the term "open," "opened," "opening," (or variations thereof) or "open state" can include both a partially open state and/or a fully open state. In certain embodiments, a quantity of heat transfer medium flowing through the pressure control valve in the closed state may be less than a quantity (e.g., flow rate) of heat transfer medium flowing through the pressure control valve when the pressure control valve is open. A quantity (e.g., flow rate) of heat transfer medium flowing through the pressure control valve when the pressure control valve is closed may correspond to about zero. The quantity (e.g., flow rate) of heat transfer medium may be greater than zero when the pressure control valve is open.

Pressure Transducer

Referring again to FIGS. 1, 2 and 4, the pressure regulation systems 52, 200 can include one or more pressure transducers, or sensors, for determining pressure of flow. The control system is arranged to receive an output from the transducer for controlling operation of the pressure regulation system. For simplicity in the following more detailed description of the transducers reference is made to the transducers shown in FIGS. 2 and 4, but any aspect of this description applies equally to sensor 66 in FIG. 1. Each pressure transducer ($PT_1$, $PT_2$, $PT_3$, $PT_4$, ... $PT_n$) can be fluidly coupled to a corresponding or associated pressure control valve ($S_1$, $S_2$, $S_3$, $S_4$, ... $S_n$). In some embodiments, the pressure transducers ($PT_1$, $PT_2$, $PT_3$, $PT_4$, ... $PT_n$) can be provided at the outlet of each pressure control valve. In other embodiments, the pressure transducers ($PT_1$, $PT_2$, $PT_3$, $PT_4$, ... $PT_n$) can be provided further downstream of the outlet of each pressure control valve ($S_1$, $S_2$, $S_3$, $S_4$, ... $S_n$). In some cases, the pressure may not vary significantly between the valve outlet (214a, 214b, 214c, 214d, ... 214n) and downstream near the body of the cryoprobe. Thus, the location of the pressure transducers ($PT_1$, $PT_2$, $PT_3$, $PT_4$, ... $PT_n$) can be customized to be a suitable location downstream of the pressure control valve ($S_1$, $S_2$, $S_3$, $S_4$, $S_n$).

The pressure transducers ($PT_1$, $PT_2$, $PT_3$, $PT_4$, ... $PT_n$) can measure a pressure of the heat transfer medium downstream (e.g., as the fluid travels toward the cryoprobe) of the corresponding pressure control valve ($S_1$, $S_2$, $S_3$, $S_4$, ... $S_n$). The pressure transducer ($PT_1$, $PT_2$, $PT_3$, $PT_4$, ... $PT_n$) can measure an instantaneous pressure of the heat transfer medium. Alternatively, the pressure transducer ($PT_1$, $PT_2$, $PT_3$, $PT_4$, ... $PT_n$) can provide a pressure reading indicative of a time-averaged pressure of the heat transfer medium over a predefined interval, such as, by sampling the pressure of the heat transfer medium over the predefined interval at a predefined sampling frequency. In such cases, the time interval over which the pressure transducer ($PT_1$, $PT_2$, $PT_3$, $PT_4$, ... $PT_n$) collects pressure data, as well as the sampling rate of data collection can be adjusted (as will be described further below). While the description below relates to the use of pressure transducers ($PT_1$, $PT_2$, $PT_3$, $PT_4$, ... $PT_n$) to provide pressure feedback to control performance, as is appreciable, the pressure transducers may provide pressure feedback to control performance during freeze cycle as well (e.g., to adjust size and shape of iceballs, etc.) In addition, the pressure transducers ($PT_1$, $PT_2$, $PT_3$, $PT_4$, ... $PT_n$) may provide an output in the form of pressure of the heat transfer medium, and/or output indicative of the pressure of the heat transfer medium (e.g., an electrical signal, voltage, etc.) One or more signal conditioning circuits (e.g., analog-digital converters, filters 324, and the like) can be optionally provided to condition the signal provided by the pressure transducers ($PT_1$, $PT_2$, $PT_3$, $PT_4$, ... $PT_n$).

Control System & Circuits

A control system is arranged to control the flow of a heat transfer medium supplied to a cryosurgical tool in order to operate the tool in one of a freezing or a thawing condition. As described herein the control controls actuation of a pressure valve arrangement and at least in a thawing condition is responsive to an output from an associated pressure transducer for controlling actuation. Further details of the control system are described below with reference to FIGS. 2 and 4 in particular but apply more generally to other embodiments.

As described previously, each pressure control valve ($S_1$, $S_2$, $S_3$, $S_4$, ... $S_n$) is fluidly connectable to at least one cryoprobe 100 so as to allow the heat transfer medium to selectively flow through the cryoprobe 100. Accordingly, certain embodiments of the system also include a control system 310 for controlling the valve controllers of the pressure control valves ($S_1$, $S_2$, $S_3$, $S_4$, ... $S_n$). The control system 310 can be a controller in the form of a processor, a gate array (e.g., field programmable gate array, FPGA), Application Specific Integrated Circuit (ASIC) or a microcontroller in electrical communication (shown by dashed lines in FIG. 1) with various components of the system. The control system 310 can include electrical and/or electronic circuitry that can be configured for, or programmable to control the operation of the valve controllers of the pressure control valves ($S_1$, $S_2$, $S_3$, $S_4$, ... $S_n$). The control system 310 can be in operative communication with pressure transducers ($PT_1$, $PT_2$, $PT_3$, $PT_4$, ... $PT_n$) and can receive pressure (or signals indicative pressure) measured therefrom.

Referring back to FIG. 2, in certain advantageous aspects, the control system 310 can be housed within the system housing 12 and in electrical communication with the pressure regulation system 200. In addition, the control system 310 can also be in electrical communication with the cryoprobes connected to the valve outlets (214a, 214b, 214c, 214d, . . . 214n). Further, the control system 310 can include and/or be in electrical communication with sensors, timers, analog/digital converters, wired or wireless communication circuits, etc. In addition, the control system 310 can be operatively connected to an external display, and input devices (e.g., keyboard, mouse, touchscreen and the like) for receiving operator input. Alternatively, the control system 310 can be an external computer connectable to the system. In such cases, the external computer can have and/or be programmed with computer readable instructions so as to perform one or more control and/or surgical steps, as will be described further below.

Figure 6:
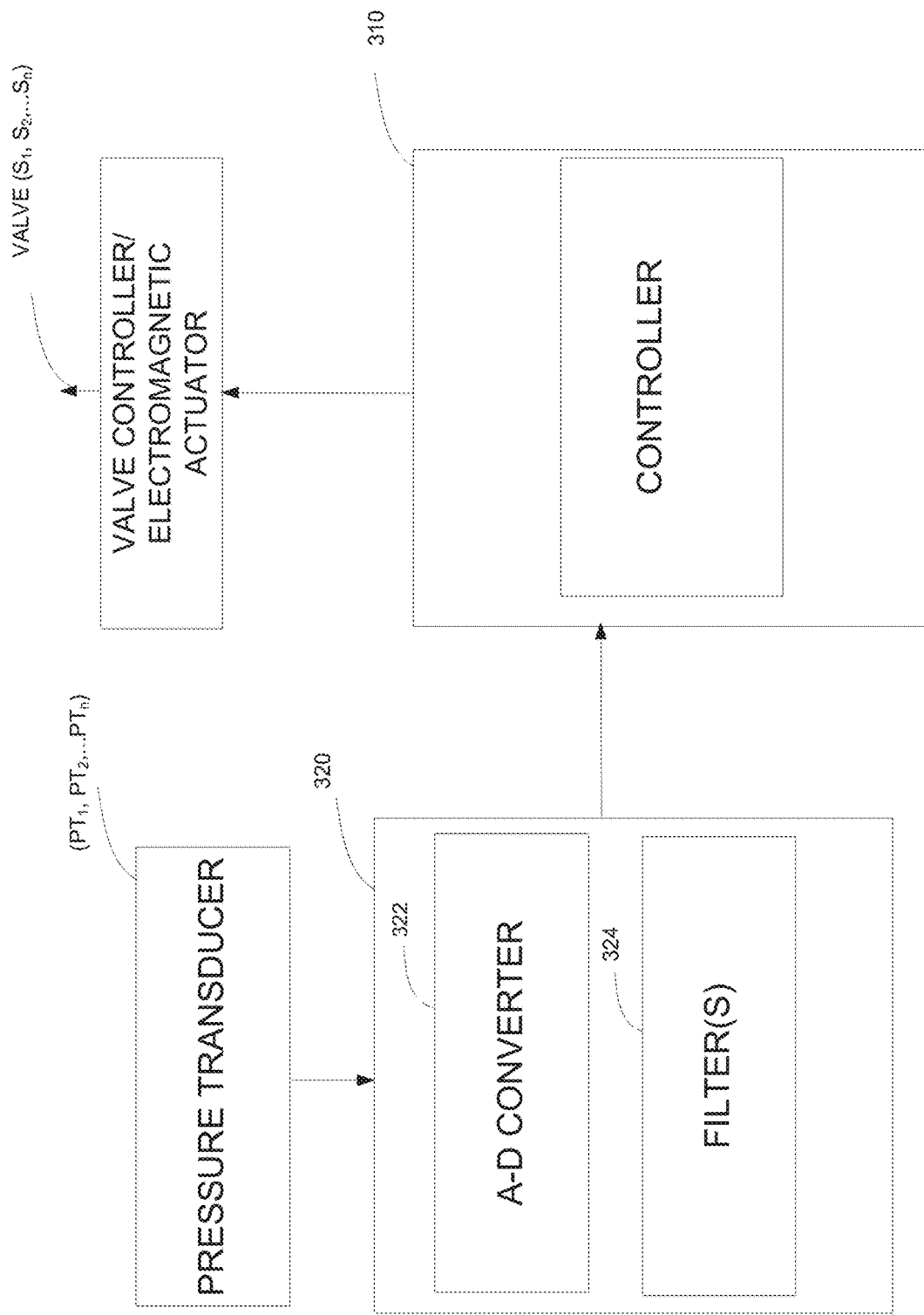
FIG. 6 is a schematic illustrating various components of the control system according to a non-limiting exemplary embodiment.

FIG. 6 is a schematic that illustrates various components of a pressure regulation system according to an embodiment. In this explanation, reference is made to the pressure regulation system 200 which comprises one or more pressure transducers ($PT_1$, $PT_2$, $PT_3$, $PT_4$, . . . $PT_n$) in electrical communication with one or more signal conditioning components 320. In an example, the signal conditioning components 320 can include an analog-digital converter 322 that converts the analog electrical signals measured by the pressure transducers ($PT_1$, $PT_2$, $PT_3$, $PT_4$, . . . $PT_n$) into a digital signal. Parameters of measurement such as sampling rate and duration over which pressure measurements (e.g., for the duration of the freeze, thaw or cautery cycle) may be set as appropriate.

With continued reference to FIG. 6, one or more filters 324 can be optionally provided as a part of the signal conditioning components 320. The filter(s) 324 can advantageously reduce measurement noise and/or provide anti-aliasing of pressure measurement.

As mentioned above and referring to FIG. 4, the control system 310 can be in electrical communication with the pressure control valves ($S_1$, $S_2$, $S_3$, $S_4$, . . . $S_n$). Accordingly, the control system 310 can send an electrical signal to the pressure control valves ($S_1$, $S_2$, $S_3$, $S_4$, . . . $S_n$) so as to transition them from the open state to the closed state or vice-versa. The control system 310 may send an electrical signal to the pressure control valves ($S_1$, $S_2$, $S_3$, $S_4$, . . . $S_n$) based on operating conditions.

In one example, if the control system 310 determines (e.g., based on operator input) that a freeze operation is to be performed, the control system 310 can send a signal to the pressure control valves ($S_1$, $S_2$, $S_3$, $S_4$, . . . $S_n$) so as to move them to the open state and/or to maintain the pressure control valves ($S_1$, $S_2$, $S_3$, $S_4$, . . . $S_n$) to be in the open state for a predefined duration (e.g., corresponding to the duration of the freeze operation). This may permit the heat transfer medium from the fluid source 14 to flow through the valve outlet (214a, 214b, 214c, 214d, . . . 214n) and into the cryoprobe 100.

In another example, if a control system determines (e.g., based on operator input) that a thaw (or cautery) operation is to be performed, the control system, for example system 310, can send a signal to the pressure control valves ($S_1$, $S_2$, $S_3$, $S_4$, . . . $S_n$) so as to repeatedly move between an open state and/or a closed state according to a predetermined algorithm. This may permit the heat transfer medium to be distributed from the fluid source 14 to the cryoprobe at a lower pressure (e.g., relative to the freeze operation).

With continued reference to FIGS. 4 and 5, in some illustrative embodiments, each cryoprobe 100 can be independently operable relative to other cryoprobes. Accordingly, the control system 310 can actuate each pressure control valve independently of the other pressure control valves. The control system 310 can thus actuate each pressure control valve selectively so as to selectively control flow of the heat transfer medium into the cryoprobe 100 corresponding to each pressure control valve. Additionally the control system 310 can actuate each valve over a certain duration, so as to supply the heat transfer medium in a cryogenic or non-cryogenic state, as will be described further below. Such embodiments can beneficially permit different types of cryoprobes (e.g., with different probe shaft outer diameters, and/or different freezing/thawing properties) to be connected to the same cryoablation system and yet be controlled independently of each other.

As described previously, the control system 310 sends an electrical signal to each pressure control valve ($S_1$, $S_2$, $S_3$, $S_4$, . . . $S_n$) to transition the pressure control valve ($S_1$, $S_2$, $S_3$, $S_4$, . . . $S_n$) into an open state or closed state. During the thaw cycle, the control system 310 can send an electrical signal to the pressure control valve ($S_1$, $S_2$, $S_3$, $S_4$, . . . $S_n$) to repeatedly switch between the open state and the closed state according to one of the disclosed control algorithms. In further advantageous embodiments, the control system 310 can actuate each pressure control valve ($S_1$, $S_2$, $S_3$, $S_4$, . . . $S_n$) selectively and independently of each other, resulting in each cryoprobe 100 being operable independently of other cryoprobes.

In one example, referring to FIGS. 2 and 5, when a first cryoprobe 100a performs the freeze operation, a second cryoprobe 100b may not perform any operation, while a third cryoprobe 100c performs the thaw operation. The control system 310 can send a first signal to a first pressure control valve $S_1$ in fluid communication with the first cryoprobe 100a to remain the open state for the duration of the freeze operation. The control system 310 can send a second signal to a second pressure control valve $S_2$ in fluid communication with the second cryoprobe 100b to remain closed, and a third signal to a third pressure control valve $S_3$, repeatedly switch between the open state and the closed state if the pressure (or data indicative of pressure) measured by the pressure transducer $PT_3$ is not within the predetermined pressure range.

As described previously, in certain embodiments, the heat transfer medium may be at a cryogenic state when leaving the supply tube 112 of the cryoprobe 100 for certain cryosurgical procedures (e.g., freeze), and in a non-cryogenic state for certain other cryosurgical procedures (e.g., thaw/cautery). In advantageous aspects of the present disclosure, the pressure control valves ($S_1$, $S_2$, $S_3$, $S_4$, . . . $S_n$) remain in the open state for the duration of the freeze procedure. However, the pressure control valves may be repeatedly opened and closed for the duration of the thaw cycle. Appreciably, repetitive opening and closing of the pressure control valves can result in a pressure reduction downstream (e.g., as the fluid travels toward the cryoprobe) of the valve outlet (214a, 214b, 214c, 214d, . . . 214n), as will be described below.

In some such embodiments, during thawing (or cautery), the pressure control valves ($S_1$, $S_2$, $S_3$, $S_4$, . . . $S_n$) can be repeatedly opened and closed until a pressure of the heat transfer medium is a desired pressure set-point (e.g., less than a second pressure). When expanding from pressures less than the second pressure, the heat transfer medium can advantageously be in a non-cryogenic state such that there may be no iceball formation during a thawing operation.

In one example, if the heat transfer medium is argon, based on the dimensions and/or freeze/thaw properties of the cryoprobe, the pressure set-point can be between about 200 psi (about 15 bar) and about 1000 psi (about 70 bar), for instance, about 500 psi (about 35 bar). Accordingly, the pressure control valves ($S_1, S_2, S_3, S_4, \ldots S_n$) can be opened and closed during the thaw/cautery procedure to effectively achieve a desired pressure in the range of pressure set-points (e.g., about 200-1000 psi, or 15-70 bar).

As described above, the pressure control valves can be opened and closed to achieve a desired pressure of the heat transfer medium. One or more control algorithms (described further below) can be used to control the opening and closing of each of the pressure control valves ($S_1, S_2, S_3, S_4, \ldots S_n$).

Control Algorithms

Algorithm 1—On-Off Control

Figure 7:
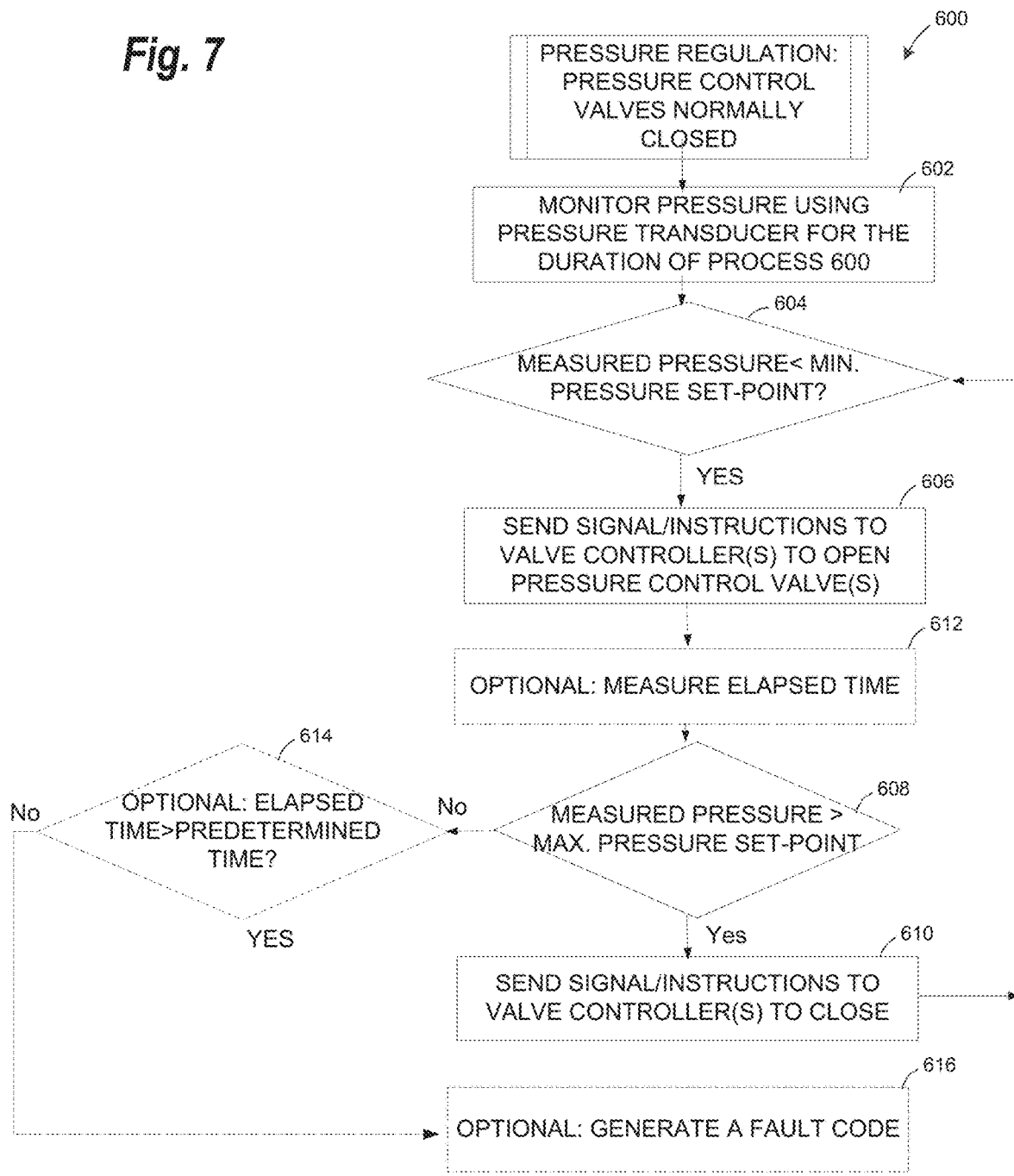
FIG. 7 is a flowchart illustrating a control algorithm for regulating pressure according to a non-limiting exemplary embodiment.

As described below, a control system (e.g. system 68 or 310) comprises a computer-readable storage medium comprising a control algorithm which, when executed by the control system, cause the control system to carry out the steps as illustrated for example in FIGS. 7 and 8 and described herein. FIG. 7 illustrates a control algorithm 600 of regulating pressure of the heat transfer medium during a thaw cycle (or cautery) according to a non-limiting exemplary embodiment. The steps described herein (e.g., for algorithms 600, 700, 900 and 1000) may be used for adjusting the pressure in at least one of the flow channels via at least one of the pressure control valves (e.g., $S_1$) based on pressures measured by at least one of the pressure transducers (e.g., $PT_1$). Optionally, the pressure in all the flow channels may be adjusted by simultaneously and/or sequentially controlling at least each of the pressure control valves ($S_1, S_2, S_3, S_4, \ldots S_n$), based on pressures measured by each of the pressure transducers ($PT_1, PT_2, PT_3, PT_4, \ldots PT_n$).

At step 602, the pressure transducer (e.g., $PT_1$) measures pressure and sends the measured pressure (or an electrical signal representative thereof) to the control system 310. The control system 310, at step 604, receives the measured pressure (or an electrical signal representative thereof) and compares it to a minimum or lower pressure set-point. If the measured pressure is less than the minimum pressure set-point value, at step 606, the control system 310 sends a signal to the valve controller to open the pressure control valve. The control system 310 may continue monitoring the pressure (via pressure received from the pressure transducer) when the valve is open to determine, at step 608, if the pressure reaches and/or exceeds a maximum, or upper pressure set-point. If the control system 310 determines that the measured pressure reaches and/or exceeds the maximum pressure set-point value, at step 610, the control system 310 sends a signal (or instructions) to the valve controller to close the pressure control valve.

In an example implementation of control algorithm 600, the pressure regulation system 200 may receive pressure from the pressure transducer at periodic intervals. For instance, the pressure transducer may sample pressure at predetermined sampling rate (e.g., 2 kHz), and may send the measured pressure to the control system 310. The sampling rate can be chosen so as to minimize (or eliminate) aliasing, and generate sufficient number of pressure readings.

The control system 310 may compare the measured pressure to the minimum and maximum pressure set-points. If the measured pressure is at or less than the pressure set-point, the control system 310 sends a signal or instructions to the valve controller to open the pressure control valve. In the meantime, the pressure transducer continues to generate a pressure measurement at its predetermined sampling rate and send to the control system 310. The control system 310 in turn, continues to monitor the measured pressure and determine whether the measured pressure is within the range pressure set-points (e.g., above minimum pressure set-point and less than maximum pressure set-point).

The minimum pressure set-point and maximum pressure set-point may be set to values based on the type of the cryoprobe and its freeze/thaw performance. The minimum and maximum pressure set-points can both be the same value or be different values. When the pressure cycles between set-points it generates an effective average flow pressure between the set-points and the values of the set-points are predetermined so that expansion from the effective average flow pressure would result in the temperature of the heat transfer medium being non-cryogenic and suitable for a thawing procedure.

In optional embodiments, the control algorithm 600 may include an optional step 612, whereby the control system 310 keeps track of time elapsed after the pressure control valve has been opened and compares the elapsed time to a predetermined time at step 614. If the elapsed time exceeds a predetermined time, at optional step 616, the control system 310 can generate a fault signal to indicate that the flow channel (one or more of 216a, 216b, 216c, 216d) has faulted if the predetermined time has elapsed. At optional step 618, the control system 310 can send a signal (or instructions) to close the pressure control valve.

In an example implementation of control algorithm 600, the pressure control valve can be opened and closed based on the measured pressure. The valve may stay open for a first duration (e.g., 30 milliseconds), at which point the pressure measured by the pressure transducer may reach the maximum pressure set-point. The control system 310 may normally send a signal to close the valve. However, if there is a fault in the pressure regulation system 200 and the control system 310 fails to close the pressure control valve, the control system 310 may continue monitoring the elapsed time since the valve was opened. If the elapsed time exceeds a predetermined time (e.g., two seconds), the control system 310 may close the pressure control valve and/or send a fault signal. Such embodiments may provide added safety in the event that the control system 310 fails to regulate the pressure.

Algorithm 2—On-Off Control with Changing Set Points

Figure 8:
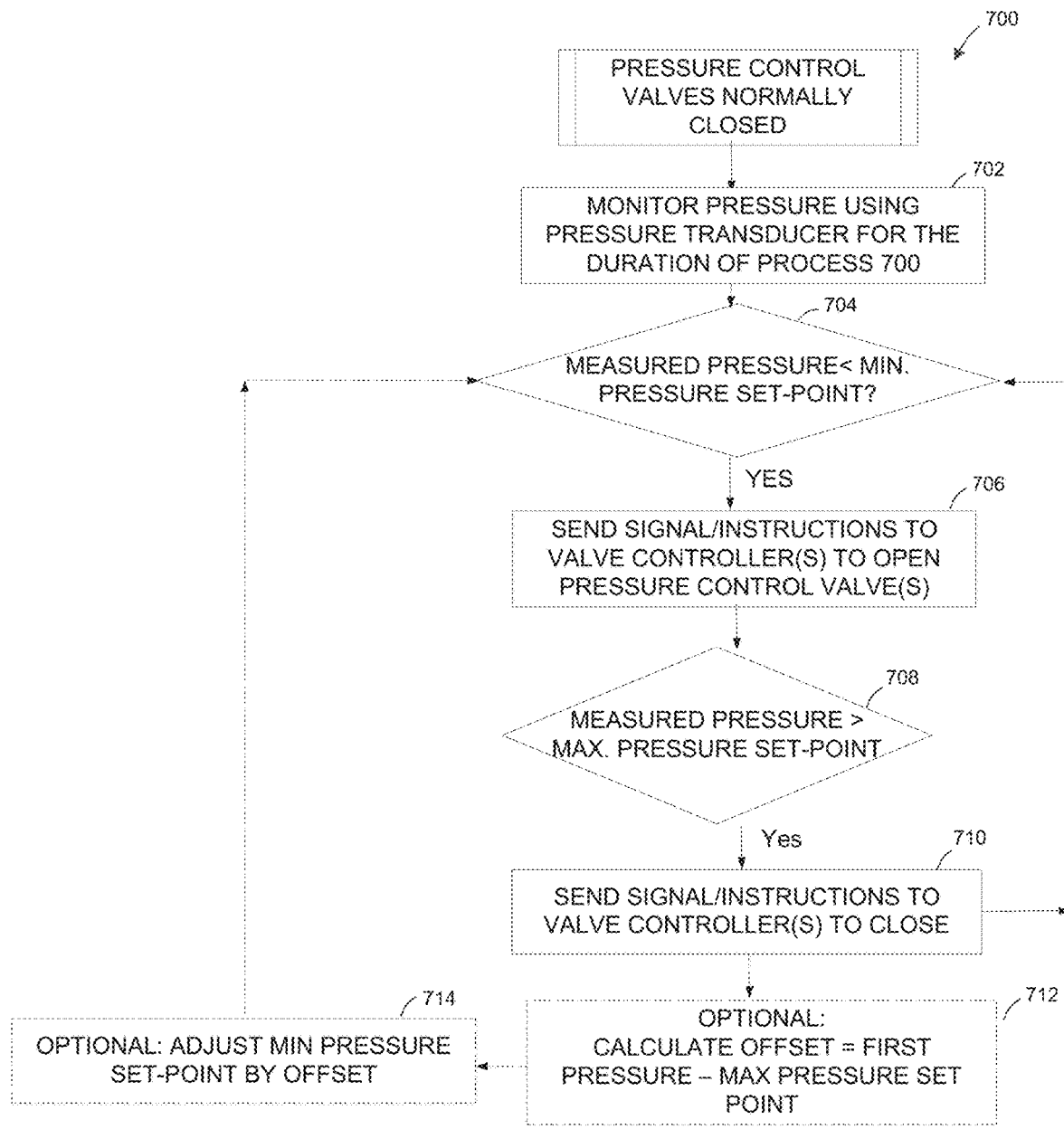
FIG. 8 is a flowchart illustrating another control algorithm for regulating pressure according to a non-limiting exemplary embodiment.

FIG. 8 illustrates a control algorithm 700 of regulating pressure of the heat transfer medium during a thaw/cautery cycle according to another non-limiting exemplary embodiment. The control algorithm 700 can be substantially similar to control algorithm 600. In one example, the control algorithm 700 may be implemented when the pressure (as measured by the pressure transducer) may not always respond instantaneously to the opening and closing of valves. Accordingly, in some such examples, the pressure (as measured by the pressure transducer) may continue rising even after the valve is closed when the pressure set-point is reached. The control algorithm 700 may address such effects to provide consistent and stable pressure.

At step 702, the pressure transducer measures pressure and sends the measured pressure (or an electrical signal representative thereof) to the control system 310. The control system 310, at step 704, receives the measured pressure (or an electrical signal representative thereof) and compares it to a minimum pressure set-point. If the measured pressure is at or less than the minimum pressure set-point, at step 706, the control system 310 sends a signal to the valve controller to open the pressure control valve. The control system 310 may continue monitoring the pressure (via pressure received from the pressure transducer) when the valve is open to determine, at step 708, if the pressure reaches and/or exceeds a maximum pressure set-point. If the control system 310 determines that the measured pressure reaches and/or exceeds the maximum pressure set-point, at step 710, the control system 310 sends a signal (or instructions) to the valve controller to close the pressure control valve. At this point, the pressure (as measured by the pressure transducer) may continue rising, before beginning to decrease. At optional step 712, the control system 310 may compare the value of pressure before the pressure began decreasing to a first pressure. If the pressure (as measured by the pressure transducer) reached and/or exceeded the first pressure (after the pressure control valves were closed), at optional step 714, the control system 310 may decide that the minimum pressure set-point may have to be offset, or adjusted, so as to result in a lower deviation from a desired nominal pressure (as will be described with respect to FIG. 9).

At step 714, the control system 310 may calculate an offset and adjust the minimum pressure set-point by an amount corresponding to the offset. In an example, the offset may be a difference between the first pressure and the maximum pressure set-point. In this example, the minimum pressure set-point may be adjusted (lowered) by the offset amount. Accordingly, for the subsequent cycle, the pressure control valve may not open until the newly-lowered, or adjusted, minimum pressure set-point is reached. In turn, the offset from the maximum set-point may also be adjusted for subsequent cycles so that the range of pressure between adjusted set-points is less compared to initial set-point values.

In some advantageous embodiments, the first pressure can be greater than the maximum pressure set-point, and the second pressure can be less than the minimum pressure set-point. In additional and alternative embodiments, the first pressure and the second pressure may not be constant throughout the thaw (or cautery) cycle, and may be adjusted each time the pressure control valve is opened and closed. In further additional and alternative embodiments, the first pressure and the second pressure may eventually, over time, equal the maximum pressure set-point and the minimum pressure set-point respectively. In such advantageous embodiments, the pressure (as measured by the pressure transducer) may eventually decrease monotonically (rather than increase initially and then decrease) after the pressure control valve is closed. In this way, the adjustment made to one or both of the set-points is reduced over pressure cycles, one cycle compared to a subsequent cycle, so that the adjustment tends to zero and the effective pressure aligns with the target nominal pressure.

In an example implementation of control algorithm 700, the pressure control valve can be opened and closed based on the measured pressure and the pressure set-points. If the pressure is below the minimum pressure set-point, the control system 310 may send a signal to open the pressure control valve. The pressure may continue increasing, and eventually reach the maximum pressure set-point. The control system 310 may send a signal to close the pressure control valve. Due to effects such as delay in valve opening and closing in response to the signals from the control system 310, blockages, etc., the pressure measured by the pressure transducer may continue increasing, for example, until the first pressure before beginning to decrease again. The first pressure can be greater than the maximum pressure set-point. Accordingly, the control system 310 may not open the pressure control valve when the minimum pressure set-point is reached if the pressure reached and/or exceeded the first pressure. The control system 310 may wait until the pressure reaches a second pressure before the pressure control valve is opened again. When the pressure reaches the second pressure, the pressure control valve is opened.

The minimum pressure set-point may be, for instance, about 450 psi (about 30 bar) in one example involving argon as the heat transfer medium. In this example, the maximum pressure set-point may be, for instance, about 500 psi (about 35 bar). The first pressure can be, for instance, about 550 psi (about 38 bar). Accordingly, the control system 310 may not open the pressure control valve when the minimum pressure set-point of about 450 psi is reached if the pressure reached and/or exceeded the first pressure of about 550 psi. In this example, the pressure continues to decrease until a second pressure of about 400 psi (about 28 bar) is reached. When the pressure reaches the second pressure, the pressure control valve is opened.

The control system 310 may dynamically adjust the values of first pressure and second pressure that correspond to valve opening and closing based on the measured pressure at subsequent cycles of valve opening and closing based on offsets between the measured pressure and the minimum and maximum pressure set-points just prior to or shortly following valve opening and valve closing respectively. Further, as will be described further below, the control system can also determine the minimum and maximum pressure set-points based on the type of the cryoprobe in operative communication therewith.

In another example, the pressure may not reach as high as the first pressure during a subsequent cycle after one cycle of pressure regulation according to control algorithm 700. After the pressure control valve is closed, the pressure may, for instance, reach a lower value of a third pressure. Accordingly, in the next subsequent cycle, the control system 310 may wait until the pressure reaches, for example, a fourth pressure before the pressure control valve is opened. In some optional advantageous embodiments, the pressures at the time of opening and closing may eventually converge to the minimum pressure set-point and maximum pressure set-point respectively. The control system 310 may dynamically adjust the values of first pressure, second pressure, third pressure and fourth pressure (as well as subsequent pressures) that correspond to valve opening and closing based on the measured pressure at various points in the cycle, and the offsets between the measured pressure and the minimum and maximum pressure set-points. Further, as will be described further below, the control system can also determine the minimum and maximum pressure set-points based on the type of the cryoprobe in operative communication therewith.

In some such examples involving argon as the heat transfer medium, if the maximum pressure set-point is about 500 psi, the first pressure is about 550 psi, the minimum pressure set-point is about 450 psi and the second pressure of about 400 psi, the third pressure can be about 525 psi (about 36 bar) and the fourth pressure can be about 475 psi (about 33 bar).

The control system 310 may normally send a signal to close the valve. However, if there is a fault in the pressure regulation system 200 and the control system 310 fails to close the pressure control valve, the control system 310 may continue monitoring the elapsed time since the valve was opened. If the elapsed time exceeds a predetermined time (e.g., two seconds), the control system 310 may close the pressure control valve and/or send a fault signal. Such embodiments may provide added safety in the event that the control system 310 fails to regulate the pressure.

FIG. 9 illustrates an example of pressure transducer data in response to opening and closing the pressure control valve. At time $t_0$, the pressure transducer begins collecting pressure data (e.g., as illustrated by steps 602 and 702 of control algorithms 600 and 700 respectively). At time $t_1$, the pressure measured by the pressure transducer (indicated by solid line in FIG. 9) is less than the minimum pressure set-point (e.g., as illustrated by steps 604 and 704 of control algorithms 600 and 700 respectively), and the control system 310 sends a signal (or instructions) to open the pressure control valve (e.g., as illustrated by steps 606 and 706 of control algorithms 600 and 700 respectively). The pressure measured by the pressure transducer begins increasing. At time $t_2$, the pressure measured by the pressure transducer reaches the maximum pressure set-point (e.g., as illustrated by steps 608 and 708 of control algorithms 600 and 700 respectively). At this point, the control system 310 sends a signal (or instructions, as illustrated, for example, by steps 610 and 710 of control algorithms 600 and 700 respectively) to close the pressure control valves.

In some optional embodiments, the pressure measured by the pressure transducer may begin decreasing monotonically following the closure of the pressure control valve until the pressure control valve is opened again. Alternatively, in other optional embodiments, the pressure measured by the pressure transducer may continue increasing (as indicated by the dashed line in FIG. 9) even after the pressure control valve has been closed until time $t_3$ before decreasing.

In some such optional embodiments, the pressure measured by the pressure transducer may reach and/or exceed a first pressure at time $t_3$. In such optional embodiments, as described above, the control system 310 may allow the pressure to continue decreasing further lower than the minimum pressure set-point to reduce the chances of pressure overshooting the maximum pressure set-point during the next instance of the pressure control valve being opened. Accordingly, the pressure (as measured by the pressure transducer) is allowed to decrease to a second pressure (less than the minimum pressure set-point) at time $t_4$, at which point the pressure control valve is opened again.

FIG. 9 also illustrates the desired nominal pressure as a solid line. The desired nominal pressure can be a cycle-average pressure and may be the pressure of the heat transfer medium downstream of the pressure control valve (e.g., when in the supply tube of the cryoprobe or downstream thereof). The desired nominal pressure may remain generally constant over time.

Also illustrated in dashed lines in FIG. 9 is an effective average pressure. The effective average pressure may be a cycle-averaged value representing a cycle-average over a single cycle. As described previously, due to effects such as delay in valve opening and closing, physical blockages, etc., pressure measured by the transducer may not instantaneously respond to the opening and closing of valves and may continue rising even after the valve is closed. Accordingly, the effective average pressure may oscillate about the desired normal pressure. Over time, as a result of the control system adjusting the valve opening and closing to ensure that measured pressures correspond to minimum and maximum pressure set-points respectively (e.g., as set forth in algorithm 700 illustrated in FIG. 8), the effective average pressure may converge (over several cycles of valve opening and valve closing) to reach the desired nominal pressure as shown in FIG. 9.

Algorithm 3—Pressure Set-Point Levels Based on Needle Type

Figure 10:
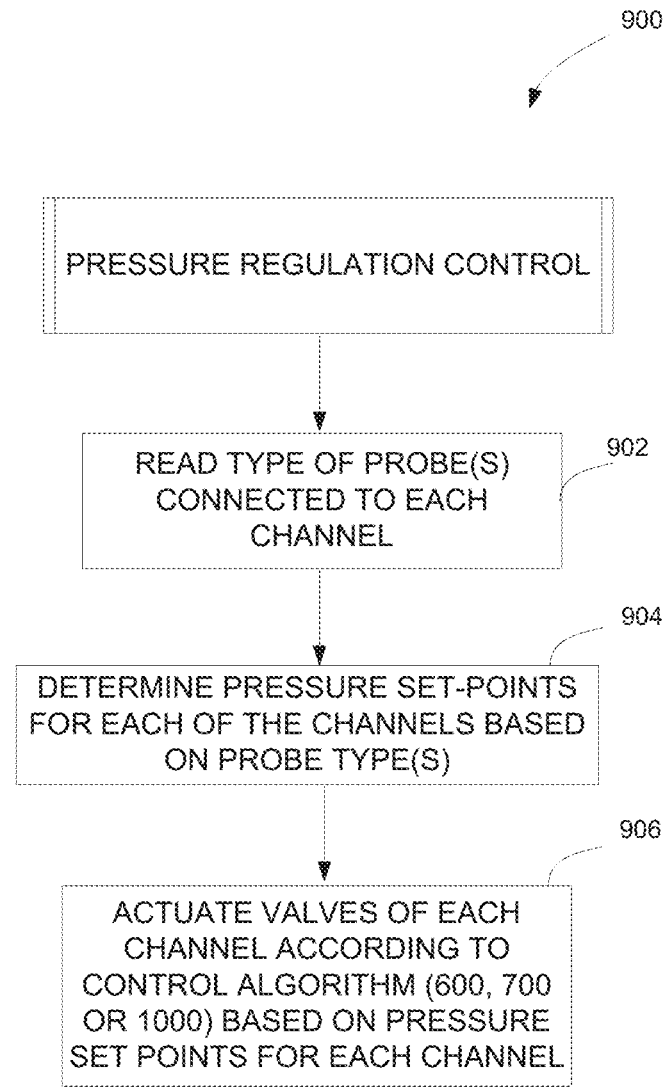
FIG. 10 is a flowchart illustrating another control algorithm for regulating pressure according to a non-limiting exemplary embodiment.
Figure 11:
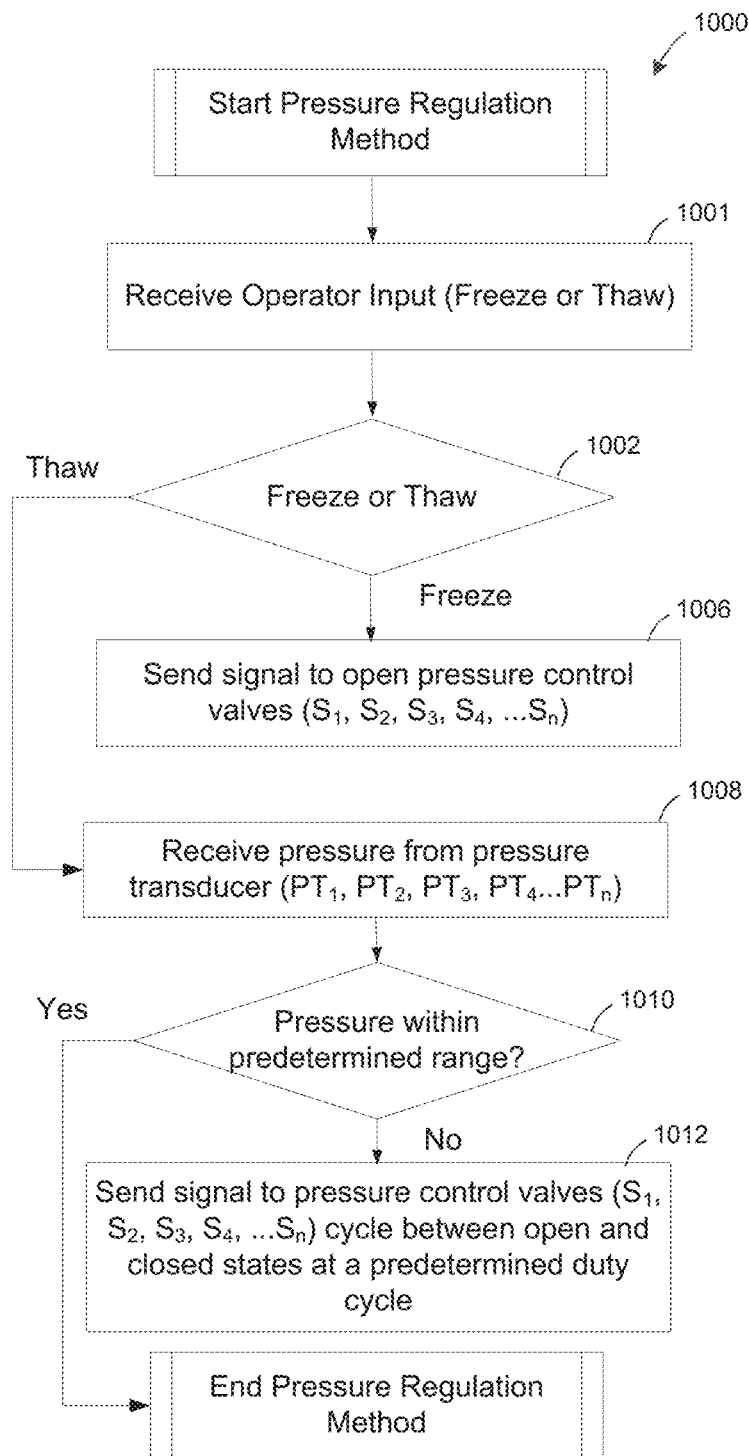
FIG. 11 is a flowchart illustrating another control algorithm for regulating pressure according to a non-limiting exemplary embodiment.

FIG. 10 illustrates a method 900 of controlling the flow of the heat transfer medium during a thaw cycle according to a non-limiting exemplary embodiment. The method 900 can advantageously permit different types of cryoprobes (e.g., with different probe shaft outer diameters, and/or different freezing/thawing properties) to be controlled independently. In such cases, the pressure set-points described above can differ. Accordingly, method 900 can determine the pressure set-points at which the heat transfer medium may have to be supplied to provide effective heat distribution during thawing (or cautery), without having freezing and/or iceball formation for a particular probe type.

At step 902 a control system such as control system 310 can (e.g., via the processor) read information regarding the cryoprobe(s) connected to each flow channel (216a, 216b, 216c, 216d, . . . 216n). The information may be stored in electronic circuitry (e.g., a chip) on the cryoprobe. The control system 310 can, at step 904, determine pressure set-points for each of the channels based on the information regarding the cryoprobe(s). In one example, optionally, the pressure set-points for different types of cryoprobes may be previously determined (e.g., experimentally) and stored in a memory or storage in operative communication (e.g., wired or wireless) with the control system 310. Alternatively, in another example, as another option, the pressure set-points may be determined empirically.

At step 906, the control system 310 can actuate the pressure control valves ($S_1$, $S_2$, $S_3$, $S_4$, . . . $S_n$) according to a control algorithm (described above, for instance, control algorithm 600 or control algorithm 700 or variants thereof) and use the pressure set-points determined at step 904. For instance, the values of maximum and minimum pressure set-points may be determined by the control system 310 at step 904, and used in conjunction with control algorithms 600 or 700. Optionally, as described above with respect to FIG. 8, the algorithm of FIG. 10 can also dynamically adjust the pressure set-points during operation, such that the measure pressure, over time, generally corresponds to a desired effective pressure.

In optional embodiments, when the method 900 is used in conjunction with control algorithm 700, the control system 310 can determine and set one or more of the maximum pressure set-point, minimum pressure set-point, first pressure and second pressure for each flow channel (one or more of 216a, 216b, 216c, 216d) based on the type of the cryoprobe connected to a corresponding flow channel and/or its freeze/thaw properties.

An example implementation of the method 900 is as follows. A first cryoprobe 100a and a second cryoprobe 100b may be connected to a first flow channel 216a and a second flow channel 216b. The control system 310 may determine (e.g., based on previous data, experiment, empirical methods) that a pressure set-point for the first cryoprobe 100a is about 500 psi and the pressure set-point for the second cryoprobe 100b is about 450 psi. In such cases, the control system 310 can actuate a first pressure control valve $S_1$ fluidly coupled to the first flow channel 216a according to the control algorithm (600, 700 or 1000) such that the pressure in the first flow channel 216a is about 500 psi. The control system 310 can also actuate the second pressure control valve $S_2$ (independently of the first pressure control valve) such that the pressure in the second flow channel 216b is about 450 psi. Additional or alternative implementations of method 900 are also contemplated.

Algorithm 3—Duty Cycling (Older Description)

FIG. 10 illustrates a control algorithm 1000 of adjusting pressure of the heat transfer medium according to a non-limiting exemplary embodiment. The method can be performed with a cryosurgical system according to any of the disclosed embodiments. The method can be in the form of machine-readable (or computer executable) instructions and provided to (e.g., programmed in the memory of) the control system 310. At step 1002, the control system 310 can determine (e.g., based on user input received at step 1001) whether the cryosurgical system is performing a thaw (or cautery) operation or a freeze operation. The control system 310 can make such a determination, for instance, based on operator input. If the control system 310 determines the system is about to perform a freeze cycle, optionally, the control system 310 can determine (based on operator input, or stored program settings), which of the cryoprobes would be performing the freeze operation. At step 1006, the control system 310 can electrically communicate with the pressure control valves ($S_1, S_2, S_3, S_4, \ldots S_n$) and send an electrical signal that switches the pressure control valves ($S_1, S_2, S_3, S_4, \ldots S_n$) from their closed state to the open state. Advantageously, at this step, the control system 310 can determine which of the pressure control valves ($S_1, S_2, S_3, S_4$, correspond to cryoprobes performing freeze operation, and selectively actuate those pressure control valves ($S_1, S_2, S_3, S_4, \ldots S_n$). Alternatively, the control system 310 can actuate all the pressure control valves ($S_1, S_2, S_3, S_4, \ldots S_n$). In further advantageous aspects, the control system 310 can control freeze performance by monitoring pressure measurement data from the pressure transducers ($PT_1, PT_2, PT_3, PT_4, \ldots PT_n$) and adjust freeze performance. For instance, the control system 310 can close (and/or repeatedly open and close) the pressure control valves ($S_1, S_2, S_3, S_4, \ldots S_n$) once a desired freeze performance (e.g., as indicated by an iceball size) is reached.

If the control system 310 determines that the cryosurgical system is performing the thaw operation (or cautery), the control system 310 receives pressure measurement data from the pressure transducers ($PT_1, PT_2, PT_3, PT_4, \ldots PT_n$) connected to the pressure control valves at step 1008. At step 1010, the control system 310 determines whether the pressure measured downstream (e.g., as the fluid travels toward the cryoprobe) of the pressure control valve is within a predetermined pressure range. As described previously, the predetermined range can be less than the second pressure (e.g., less than which the heat transfer medium is in a non-cryogenic state). If the control system 310 determines that the pressure is not within the predetermined pressure range, at step 1012, the control system 310 actuates (e.g., by sending an electrical signal) the pressure control valves repeatedly so as to switch between open state and closed state of the pressure control valves. The control system 310 can perform this step until the pressure downstream (e.g., as the fluid travels toward the cryoprobe) of the pressure control valve is within the predetermined pressure range.

In advantageous aspects of the control algorithm 1000, the control system 310 can actuate the pressure control valve over several repeated cycles during the thaw process (or cautery), wherein for each cycle, the pressure control valve is in the open state for a first time interval and in the closed state for a second time interval. The first and second time intervals can be chosen to result in desired pressure downstream of the pressure control valve(s). In certain additional embodiments, the pressure control valve(s) can be in the open state for a duration corresponding to the freeze operation. In some embodiments, the ratio of a time over which the pressure control valve of the one or more pressure control valves remains open relative to a time over which the pressure control valve of the one or more pressure control valves remains closed can be between about 5% and about 80%.

Embodiments according to the present disclosure provide several advantages. Embodiments provide the ability to use a single heat transfer medium for both freeze and thaw (or cautery) operations, thereby eliminating additional fluid sources. Further, by using the heat transfer medium to distribute heat during the thaw cycle (or cautery), heat generated by the heaters within cryoprobe can be more evenly distributed such that temperatures measured at various points along a length of the cryoprobe may not vary drastically. Certain embodiments permit adjusting the pressure of the heat transfer medium over a wide range without the use of additional pressure regulators or solenoids. Several of the disclosed embodiments provide a compact and efficiently packaged cryoablation system.

Non-limiting embodiments have been described. These and further embodiments are within the scope of the following claims.

The invention claimed is:

1. A pressure regulation system for a surgical system for regulating a pressure of a heat transfer medium supplied to a surgical tool from a heat transfer medium source, the surgical tool being connectable to the surgical system, the pressure regulation system comprising: a pressure control valve, the pressure control valve comprising an inlet being fluidly connectable to the heat transfer medium source, and an outlet being fluidly connectable to the surgical tool, the pressure control valve being actuable so as to be in an open state so as to permit passage of the heat transfer medium therethrough; and a closed state so as to reduce the passage of the heat transfer medium therethrough, wherein a quantity of heat transfer medium flowing through the pressure control valve in the closed state is less than a quantity of heat transfer medium flowing through the pressure control valve in the open state; and a control system operatively coupled to the pressure control valve, the control system being configured to: receive a signal corresponding to a pressure of the heat transfer medium at or downstream of the outlet of the pressure control valve, determine whether the pressure is at or less than a minimum pressure set-point, if the control system determines that the pressure is at or less than the minimum pressure set-point, send a first signal to actuate the pressure control valve to the open state, determine whether the pressure is above a maximum pressure set-point, and if the control system determines that the pressure is above the maximum pressure set-point, send a second signal to actuate the pressure control valve to the closed state;

wherein the control system is configured to determine if the pressure increases to a first pressure exceeding the maximum set-point pressure after the pressure control valve is actuated to a closed state, and to adjust the minimum pressure set-point by an offset equal to a difference between the first pressure and the maximum pressure set-point.

2. A cryosurgical system, comprising: one or more cryoprobes; one or more pressure control valves, each pressure control valve being fluidly coupled with at least one cryoprobe, each pressure control valve being independently actuable with respect to other pressure control valves so as to be in an open state so as to permit passage of the heat transfer medium therethrough; and a closed state so as to reduce the passage of the heat transfer medium therethrough, wherein a quantity of heat transfer medium flowing through the pressure control valve in the closed state is less than a quantity of heat transfer medium flowing through the pressure control valve in the open state; one or more pressure transducers, each pressure transducer being fluidly coupled to a corresponding pressure control valve; and a control system in operative communication with each pressure control valve, the control system being configured to: determine whether at least one cryoprobe is performing a freeze operation or a thaw operation; if the control system determines that the at least one cryoprobe is performing the freeze operation, open the pressure control valve fluidly coupled to the at least one cryoprobe, such that a heat transfer medium is supplied through the pressure control valve to the at least one cryoprobe, so as to result in cryogenic expansion and/or freezing, and if the control system determines that the at least one cryoprobe is performing the thaw operation, actuate the pressure control valve to repeatedly open and close the pressure control valve fluidly coupled to the at least one cryoprobe based on pressure measured by the pressure transducer, such that the pressure of the heat transfer medium supplied through the pressure control valve is less than a pressure corresponding to cryogenic expansion and/or freezing produced from the heat transfer medium, wherein the control system is configured to actuate each pressure control valve independently of other pressure control valves based on pressure measured by each of the pressure transducer fluidly coupled to the corresponding pressure control valve, and wherein the control system is configured to determine if the pressure increases to a first pressure exceeding the maximum set-point pressure after the pressure control valve is actuated to a closed state, and to adjust the minimum pressure set-point by an offset equal to a difference between the first pressure and the maximum pressure set-point.

3. The pressure regulation system of claim 1, wherein the control system is configured to send a third signal to actuate the pressure control valve to an open state if the control system determines, after the pressure control valve is actuated to a closed state, that the pressure is at or less than the adjusted value of the minimum pressure set-point.

4. The pressure regulation system of claim 1, wherein the control system is configured to measure an elapsed time after the pressure control valve is actuated to an open state, and compare the elapsed time to a predetermined time.

5. The pressure regulation system of claim 4, wherein the control system is configured to send the second signal to actuate the pressure control valve to a closed state if the elapsed time exceeds the predetermined time.

6. The pressure regulation system of claim 4, wherein the control system is configured to send a fourth signal indicative of a fault condition, if the elapsed time exceeds the predetermined time.

7. The pressure regulation system of claim 1, wherein the pressure control valve is co-operable with a valve actuator and the valve actuator is responsive to a control signal from the control system for actuated the valve to an open state and to a closed state.

8. The pressure regulation system of claim 7, wherein the actuator comprises a solenoid.

9. The pressure regulation system of claim 1, further comprising a pressure transducer configured to measure the pressure of the heat transfer medium at the outlet or downstream of the outlet of the pressure control valve.

10. A cryosurgical system, comprising: one or more cryoprobes for insertion in a patient for performing a cryosurgical procedure, each cryoprobe being configured to receive a heat transfer medium conveyed from a source of heat transfer medium; a pressure regulation system for regulating the pressure of a heat transfer medium conveyed to the or each cryoprobe, comprising: one or more pressure control valves, each pressure control valve being operable to place the source of heat transfer medium in fluid communication with at least one cryoprobe, each pressure control valve being actuable so as to be in an open state so as to permit passage of the heat transfer medium therethrough, or in a closed state so as to reduce passage of the heat transfer medium therethrough, wherein a quantity of heat transfer medium flowing through the pressure control valve in the closed state is less than a quantity of heat transfer medium flowing through the pressure control valve in the open state, and one or more pressure transducers, each pressure transducer being configured to measure a pressure of the heat transfer medium at or downstream of an associated pressure control valve; and a control system operably connected to said one or more pressure control valves and said one or more pressure transducers, and configured to: determine if the pressure received from a said pressure transducer is at or less than a minimum pressure set-point, send a first signal to actuate an associated pressure control valve to an open state if the pressure is at or less than the minimum pressure set-point, determine if the pressure received from a said pressure transducer is at or greater than a maximum pressure set-point, and send a second signal to actuate an associated pressure control valve to a closed state if the pressure is greater than the maximum pressure set-point;

wherein the control system is configured to determine if the pressure increases to a first pressure exceeding the maximum set-point pressure after the pressure control valve is actuated to a closed state, and to adjust the minimum pressure set-point by an offset equal to a difference between the first pressure and the maximum pressure set-point.

11. The cryosurgical system of claim 10, comprising a plurality of said cryoprobes and wherein each cryoprobe is independently operable relative to other cryoprobes, such that the control system is arranged to determine the maximum pressure set-point and the minimum pressure set-point corresponding to each cryoprobe, and to actuate to an open state and a closed state the pressure control valves connected to respective cryoprobes based on the corresponding maximum pressure set-point and the minimum pressure set-point.

12. The cryosurgical system of claim 10, wherein each pressure control valve comprises a valve actuator for actuating the valve to a closed state and an open state and the actuator is responsive to a control signal from the control system for controlling actuation.

13. The cryosurgical system of claim 10, wherein each cryoprobe comprises an electrical heater responsive to a control signal from the control system for heating a heat transfer medium in the cryoprobe during a thaw operation.

14. The cryosurgical system of claim 13, wherein the control system is arranged to regulate the pressure of heat transfer medium conveyed to the or each cryoprobe in a thaw operation so that the pressure is at or lower than the maximum pressure set-point at which the heat transfer medium is in a non-cryogenic state for distributing heat generated by the electrical heater for transfer to a patient.

15. The cryosurgical system of claim 10, wherein the control system is arranged to regulate the pressure of heat transfer medium conveyed to the or each cryoprobe so that the pressure is greater than the maximum pressure set-point at which the heat transfer medium is in a cryogenic state to freeze and/or cryogenically ablate tissue surrounding the cryoprobe during a freeze operation.

16. The cryosurgical system of claim 15, wherein the control system is arranged to cause each pressure control valve to be actuated to an open state for the duration of the freeze operation.

17. The cryosurgical system of claim 10, wherein the heat transfer medium is argon.

18. The cryosurgical system of claim 17, arranged for fluid communication with a source of heat for supplying heat transfer medium at a pressure of between about 1000 psi (about 70 bar) and about 4000 psi (about 275 bar) upstream of the pressure regulation system.

19. The cryosurgical system of claim 18, wherein the minimum pressure set-point is at least about 200 psi (about 15 bar).

20. The cryosurgical system of claim 18, wherein the maximum pressure set-point is at or below about 1000 psi (about 70 bar).

21. The cryosurgical system of claim 10, wherein, when the pressure received from the pressure transducer of the one or more pressure transducers is at or greater than a maximum pressure set-point, the control system sends a signal to decrease the ratio of a time over which the pressure control valve of the one or more pressure control valves remains open relative to a time over which the pressure control valve of the one or more pressure control valves remains closed.

22. A method of adjusting pressure in a cryoprobe, comprising: providing a cryosurgical system, comprising one or more cryoprobes, one or more pressure control valves, each pressure control valve being fluidly coupled with at least one cryoprobe, one or more pressure transducers, each pressure transducer being fluidly coupled to a corresponding pressure control valve, and a control system in operative communication with each pressure control valve; determining whether at least one cryoprobe is performing a freeze operation or a thaw operation; if the at least one cryoprobe is performing the freeze operation, opening the pressure control valve fluidly coupled to the at least one cryoprobe, such that a heat transfer medium is supplied through the pressure control valve to the at least one cryoprobe, so as to result in cryogenic expansion and/or freezing, and if the at least one cryoprobe is performing the thaw operation, actuating the pressure control valve to repeatedly open and close the pressure control valve fluidly coupled to the at least one cryoprobe based on pressure measured by the pressure transducer, such that the pressure of the heat transfer medium supplied through the pressure control valve is less than a pressure corresponding to cryogenic expansion and/or freezing produced from the heat transfer medium, wherein the control system actuates each pressure control valve independently of other pressure control valves based on pressure measured by each of the pressure transducer fluidly coupled to the corresponding pressure control valve, and wherein the control system is configured to determine if the pressure increases to a first pressure exceeding the maximum set-point pressure after the pressure control valve is actuated to a closed state, and to adjust the minimum pressure set-point by an offset equal to a difference between the first pressure and the maximum pressure set-point.

* * * * *